United States Patent
Patil et al.

(10) Patent No.: US 10,501,464 B2
(45) Date of Patent: Dec. 10, 2019

(54) 7-OXO-6-(SULFOOXY)-1,6-DIAZABICYCLO [3.2.1]OCTANE-2-CARBOXAMIDE CONTAINING COMPOUNDS AND THEIR USE IN TREATING BACTERIAL INFECTIONS

(71) Applicant: WOCKHARDT LIMITED, Chikalthana, Aurangabad (IN)

(72) Inventors: Vijaykumar Jagdishwar Patil, Solapur (IN); Sudhir Shengule, Aurangabad (IN); Mangesh Pawar, Maharashtra (IN); Rajib Bhuniya, Burdwan (IN); Zaki Ahmed Burhanuddin Munshi, Mumbai (IN); Prashant Ratnakar Joshi, Maharashtra Parbhani (IN); Swapna Shripad Takalkar, Maharashtra (IN); Mahesh Vithalbhai Patel, Maharashtra (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/781,121

(22) PCT Filed: Dec. 8, 2016

(86) PCT No.: PCT/IB2016/057426
§ 371 (c)(1),
(2) Date: Jun. 2, 2018

(87) PCT Pub. No.: WO2017/098425
PCT Pub. Date: Jun. 15, 2017

(65) Prior Publication Data
US 2019/0016720 A1    Jan. 17, 2019

(30) Foreign Application Priority Data
Dec. 11, 2015   (IN) .......................... 4667/MUM/2015

(51) Int. Cl.
C07D 471/08   (2006.01)
A61K 31/439   (2006.01)
A61P 31/04    (2006.01)

(52) U.S. Cl.
CPC ............ *C07D 471/08* (2013.01); *A61P 31/04* (2018.01)

(58) Field of Classification Search
CPC .................................................. C07D 471/108
See application file for complete search history.

(56) References Cited

FOREIGN PATENT DOCUMENTS

| EP | 2857401 | 4/2015 |
|----|---------|--------|
| WO | WO/2014/091268 | 6/2014 |
| WO | WO/2015/063714 | 5/2015 |

OTHER PUBLICATIONS

Burger's Medicinal Chemistry,edited by Manfred E. Wolff, 5th Ed. Part 1, pp. 975-977 (1995). (Year: 1995).*
Banker et al. "Modern Pharmaceutics", 3rd Ed. p. 596 (1996). (Year: 1996).*
Testa et al. Pure Appl. Chem. vol. 76, pp. 907-914 (2004). (Year: 2004).*
Jim O'Neil's publication, 2016. UK government report on antimicrobial resistance (AMR), (1 page).
Nature Biotechnology vol. 36 No. 7 Jul. 2018, p. 555.
Woldu. Title: Klebsiella pneumoniae and Its Growing Concern in Healthcare Settings. Clin Exp Pharmacol 2016, 6:1, (7 pages).

* cited by examiner

*Primary Examiner* — Emily A Bernhardt
(74) *Attorney, Agent, or Firm* — Bio Intellectual Property Services; O. (Sam) Zaghmout

(57) ABSTRACT

Compounds of Formula (I), their preparation, and use in preventing or treating a bacterial infection are disclosed.

Formula (I)

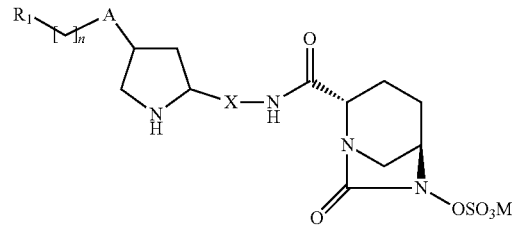

16 Claims, No Drawings

7-OXO-6-(SULFOOXY)-1,6-DIAZABICYCLO [3.2.1]OCTANE-2-CARBOXAMIDE CONTAINING COMPOUNDS AND THEIR USE IN TREATING BACTERIAL INFECTIONS

PRIORITY APPLICATION(S)

This application claims priority to Indian Patent Application No. 4667/MUM/2015 filed on Dec. 11, 2015, the disclosures of which is incorporated herein by reference in its entirety as if fully rewritten herein.

FIELD OF THE INVENTION

The invention relates to 7-oxo-6-(sulfooxy)-1,6-diazabicyclo[3.2.1]loctane-2-carboxamide containing compounds containing compounds, their preparation and their use in preventing or treating infections.

BACKGROUND OF INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistant. Coates et al. (Br. J. Pharmacol. 2007; 152(8), 1147-1154.) have reviewed novel approaches to developing new antibiotics. However, the development of new antibacterial agents is a challenging task. For example, Gwynn et al. (Annals of the New York Academy of Sciences, 2010, 1213: 5-19) have reviewed the challenges in discovery of antibacterial agents.

Several antibacterial agents have been described in the prior art (for example, see PCT International Application Nos. PCT/US2010/060923, PCT/EP2010/067647, PCT/US2010/052109, PCT/US2010/048109, PCT/GB2009/050609, PCT/FR01/02418, PCT/EP2009/056178, PCT/US52009/041200, PCT/IB2012/054290, PCT/IB 2013/053092, PCT/IB 2012/054296, PCT/IB2012/054706, PCT/JP2013/064971, PCT/IB2012/002675, PCT/US2013/034562 and PCT/US2013/034589). However, there remains a need for development of antibacterial agents for preventing and/or treating bacterial infections, including those caused by bacteria that are resistant to known antibacterial agents.

The inventors have now surprisingly discovered novel 7-oxo-6-(sulfooxy)-1,6-diazabicyclo[3.2.1]octane-2-carboxamide containing compounds having antibacterial activity.

SUMMARY OF THE INVENTION

Accordingly, there are provided 7-oxo-6-(sulfooxy)-1,6-diazabicyclo[3.2.1]octane-2-carboxamide containing compounds, methods for preparation of these compounds, pharmaceutical compositions comprising these compounds, and methods for preventing or treating bacterial infection in a subject using these compounds.

In one general aspect, there are provided compounds of Formula (I):

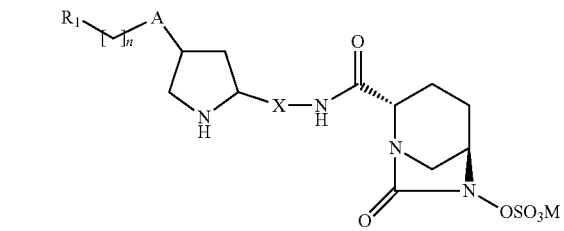

Formula (I)

or a stereoisomer or a pharmaceutically acceptable derivative thereof;

Wherein:

is selected from —$CH_2$—O— or —(C=O)—NH—;

A is heterocycloalkyl or heteroaryl optionally substituted with one or more substituents selected from $C_1$-$C_6$ alkyl, $NR_2R_3$, aryl, heteroaryl, cycloalkyl or heterocycloalkyl;

$R_1$ is selected from:
(a) hydrogen,
(b) $C_1$-$C_6$ alkyl optionally substituted with one or more substituents independently selected from $OR_2$, $NR_2R_3$, $SR_2$, halogen, CN, $COOR_2$, $CONR_2R_3$, $SR_2$, $CH_2OR_2$ or $CH_2NR_2R_3$, aryl, heteroaryl, cycloalkyl or heterocycloalkyl,
(c) halogen,
(d) CN,
(e) $CONR_2R_3$,
(f) $COOR_2$,
(g) CHO,
(h) $NR_2R_3$,
(i) $NHCOOR_2$,
(j) $SR_2$,
(k) $SOR_2$,
(l) $SO_2R_2$,
(m) aryl,
(n) heteroaryl,
(o) cycloalkyl, or
(p) heterocycloalkyl;

$R_2$ and $R_3$ are each independently selected from:
(a) hydrogen,
(b) $C_1$-$C_6$ alkyl,
(c) cycloalkyl,
(d) heterocycloalkyl,
(e) aryl, or
(f) heteroaryl;

n is 0, 1, 2, 3 or 4;

M is hydrogen or a cation.

In one general aspect, there are provided pharmaceutical compositions comprising a compound of Formula (I) or a stereoisomer or a pharmaceutically acceptable derivative thereof.

In another general aspect, there are provided methods for preventing or treating a bacterial infection in a subject, said methods comprising administering to said subject a pharmaceutically effective amount of a compound of Formula (I) or a stereoisomer or a pharmaceutically acceptable derivative thereof.

In another general aspect, there are provided methods for preventing or treating a bacterial infection in a subject, said methods comprising administering to said subject a pharmaceutically effective amount of a pharmaceutical composition comprising a compound of Formula (I) or a stereoisomer, or a pharmaceutically acceptable derivative thereof.

In yet another general aspect, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In another general aspect, there are provided a methods for preventing or treating a bacterial infection in a subject, said methods comprising administering to said subject a pharmaceutically effective amount of a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In another general aspect, there are provided methods for preventing or treating a bacterial infection in a subject, said methods comprising administering to said subject a pharmaceutically effective amount of: (a) a compound of Formula (I) or a stereoisomer or a pharmaceutically acceptable derivative thereof, and (b) at least one antibacterial agent or a pharmaceutically acceptable derivative thereof.

In yet another general aspect, there are provided methods for increasing antibacterial effectiveness of an antibacterial agent in a subject, said methods comprising co-administering said antibacterial agent or a pharmaceutically acceptable derivative thereof with a compound of Formula (I) or a stereoisomer or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The inventors have surprisingly discovered 7-oxo-6-(sulfooxy)-1,6-diazabicyclo[3.2.1]octane-2-carboxamide containing compounds containing compounds having antibacterial properties.

The term "$C_1$-$C_6$ alkyl" as used herein refers to branched or unbranched acyclic hydrocarbon radical with 1 to 6 carbon atoms. Typical non-limiting examples of "$C_1$-$C_6$ alkyl" include methyl, ethyl, n-propyl, iso-propyl, n-butyl, sec-butyl, iso-butyl, tert-butyl, n-pentyl, iso-pentyl, tert-pentyl, neopentyl, sec-pentyl, 3-pentyl, n-hexyl, 2-methylpentyl, 3-methylpentyl, 2,2-dimethylbutyl, 2,3-dimethylbutyl and the like. The "$C_1$-$C_6$ alkyl" may be unsubstituted, or substituted with one or more substituents. Typical, non-limiting examples of such substituents include halogen, alkoxy, CN, SH, COOH, $COOC_1$-$C_6$alkyl, $CONH_2$, OH, $NH_2$, $NHCOCH_3$, cycloalkyl, heterocycloalkyl, heteroaryl, aryl and the like.

The term "cycloalkyl" as used herein refers to three to seven member cyclic hydrocarbon radicals. The cycloalkyl group optionally incorporates one or more double or triple bonds, or a combination of double or triple bonds, but which is not aromatic. Typical, non-limiting examples of cycloalkyl groups include cyclopropyl, cyclobutyl, cyclopentyl, cyclohexyl, and cycloheptyl. The cycloalkyl may be unsubstituted, or substituted with one or more substituents. Typical, non-limiting examples of such substituents include $C_1$-$C_6$ alkyl, halogen, alkoxy, CN, SH, COOH, $COOC_1$-$C_6$alkyl, $CONH_2$, OH, $NH_2$, $NHCOCH_3$, heterocycloalkyl, heteroaryl, aryl, $SO_2$-alkyl, $SO_2$-aryl, $OSO_2$-alkyl, $OSO_2$-aryl and the like.

The term "aryl" as used herein refers to a monocyclic or polycyclic aromatic hydrocarbon. Typical, non-limiting examples of aryl groups include phenyl, naphthyl, anthracenyl, flourenyl, phenanthrenyl, indenyl and the like. The aryl group may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heterocycloalkyl, heteroaryl, aryl, $SO_2$-alkyl, $SO_2$-aryl, $OSO_2$-alkyl, $OSO_2$-aryl and the like. The term "aryl" includes six to fourteen membered monocyclic or polycyclic aromatic hydrocarbon.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include pyridyl, pyrimidinyl, pyrazinyl, pyridazinyl, triazinyl, furanyl, pyrrolyl, thienyl, oxadiazolyl, thiadiazolyl, tetrazolyl, oxazolyl, thiazolyl, imidazolyl, pyrazolyl, triazonyl, isoxazolyl, oxadiazolyl, oxatriazolyl, isothiazolyl, thiatriazolyl, thiazinyl, oxazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-pyridazinyl, purinyl, benzofuranyl, isobenzofuranyl, benzothienyl, benzothiophenyl, carbazolyl, benzimidazolyl, benzoxazolyl, benzoisoxazolyl, benzothiazolyl, benzotriazolyl, indolyl, isoindolyl, quinolinyl, isoquinolinyl, acridinyl, naphthothienyl, thianthrenyl, chromenyl, xanthenyl, phenoxathienyl, indolizinyl,indazolyl, phthalazinyl, naphthyridinyl, qinoxalinyl, quinazolinyl, cinnolinyl, pteridinyl, beta-carbolinyl, phenanthridinyl, phenanthrolinyl, phenazinyl, phenothiazinyl, phenoxazinyl and the like. The heteroaryl group may be unsubstituted, or substituted with one or more substituents. Typical, non-limiting examples of such substituents include $C_1$-$C_6$ alkyl, halogen, alkoxy, CN, COOH, $CONH_2$, OH, SH, $SCH_3$, $NH_2$, $NHCOCH_3$, heterocycloalkyl, heteroaryl, aryl, $SO_2$-alkyl, $SO_2$-aryl, $OSO_2$-alkyl, $OSO_2$-aryl and the like. The term "heteroaryl" includes five to fourteen membered monocyclic or polycyclic aromatic hydrocarbon group containing at least one heteroatom selected from nitrogen, oxygen, and sulfur.

The term "heterocycloalkyl" as used herein refers to three to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting example of heterocycloalkyl groups include aziridinyl, azetidinyl, oxazetidinyl, pyrrolidinyl, 2-oxo-pyrrolidinyl, pyrazolidinyl, imidazoidinyl, imidazolidin-2-one-yl, oxazolidinyl, thiazolidinyl, piperidinyl, oxazinyl, thiazinyl, piperazinyl, piperazin-2,3-dione-yl, morpholinyl, thiomorpholinyl, azepanyl, and the like. The heterocycloalkyl may be unsubstituted, or substituted with one or more substituents. Typical, non-limiting examples of such substituents include $C_1$-$C_6$ alkyl, halogen, alkoxy, CN, COOH, $CONH_2$, OH, $NH_2$, $NHCOCH_3$, heteroaryl, aryl, $SO_2$-alkyl, $SO_2$-aryl, $OSO_2$-aryl and the like. The term "heterocycloalkyl" includes three to seven membered cycloalkyl containing at least one heteroatom selected from nitrogen, oxygen, and sulfur.

The term "halogen" or halo as used herein refers to chlorine, bromine, fluorine or iodine.

The term "Boc" as used herein refers to tert-butyloxycarbonyl group.

The term "EDC. HCl" as used herein refers to 1-ethyl-3-(3-dimethylaminopropyl)carbodiimide hydrochloride.

The term "HOBt" as used herein refers to hydroxybenzotriazole.

The term "Nosyl chloride" as used herein refers to 4-nitro benzene sulfonyl chloride.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salts, pro-drugs, metabolites, esters, ethers, hydrates, polymorphs, solvates, complexes, and adducts) which, upon administration to a subject, are capable of providing (directly or indirectly) the antibacterial agent.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irrigation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutical acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulfonic acid or the like. Alternatively, the acid moiety may be converted into its salt by treating with a suitable base. Typical non-limiting examples of such bases include sodium carbonate, sodium bicarbonate, sodium ethylhexanoate, potassium carbonate, potassium bicarbonate, potassium ethyl hexanoate or the like. In case of compounds containing more than one functional group capable of being converted into salt, each such functional group may be converted to salt independently. For example, in case of compounds containing two basic nitrogen atoms, one of the basic nitrogen can form salt with one acid while the other basic nitrogen can form salt with another acid. Some compounds according to the invention contain both acidic as well as basic moieties, and thus can form inner salts or corresponding zwitterions. In general, all pharmaceutically acceptable salt forms of compound of Formula (I) according to invention including acid addition salts, base addition salts, zwitterions or the like are contemplated to be within the scope of the present invention and are generically referred to as pharmaceutically acceptable salts.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of other floras, which are not desirable. The term "infection" includes infection caused by bacteria.

The term "treat", "treating" or "treatment" as used herein refers to administration of a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions, or one or more of pharmaceutically active ingredients discussed herein, with or without additional pharmaceutically active or inert ingredients, in order to: (i) reduce or eliminate either a bacterial infection, or one or more symptoms of a bacterial infection, or (ii) retard progression of a bacterial infection, or one or more symptoms of a bacterial infection, or (iii) reduce severity of a bacterial infection, or one or more symptoms of a bacterial infection, or (iv) suppress clinical manifestation of a bacterial infection, or (v) suppress manifestation of adverse symptoms of a bacterial infection.

The terms "pharmaceutically effective amount" or "therapeutically effective amount" or "effective amount" as used herein refer to an amount, which has a therapeutic effect or is the amount required to produce a therapeutic effect in a subject. For example, a "therapeutically effective amount"

or "pharmaceutically effective amount" or "effective amount" of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). Such effective amount depends on several factors, including but not limited to, the microorganism (e.g. bacteria) involved, characteristics of the subject (for example height, weight, sex, age and medical history), severity of infection and particular type of the antibacterial agent used. For prophylactic treatments, a prophylactically effective amount is that amount which would be effective in preventing the bacterial infection.

The term "administration" or "administering" refers to and includes delivery of a composition, or one or more pharmaceutically active ingredients to a subject, including for example, by any appropriate method, which serves to deliver the composition or its active ingredients or other pharmaceutically active ingredients to the site of infection. The method of administration may vary depending on various factors, such as for example, the components of the pharmaceutical composition or type/nature of the pharmaceutically active or inert ingredients, site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intra respiratory, intraperitoneal, intramuscular, parenteral, sublingual, transdermal, intranasal, aerosol, intraocular, intratracheal, intra rectal, vaginal, gene gun, dermal patch, eye drop and mouthwash. In case of a pharmaceutical composition comprising more than one ingredients (active or inert), one of the ways of administering such composition is by admixing the ingredients (e.g. in the form of a suitable unit dosage form such as tablet, capsule, solution, powder or a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term "growth" also includes maintenance of on-going metabolic processes of the microorganism, including the processes that keep the microorganism alive.

The term, "effectiveness" as used herein refers to ability of a treatment, or a composition, or one or more pharmaceutically active ingredients to produce a desired biological effect in a subject. For example, the term "antibacterial effectiveness" of a composition or of an antibacterial agent refers to the ability of the composition or the antibacterial agent to prevent or treat bacterial infection in a subject.

The term "synergistic" or "synergy" as used herein refers to the interaction of two or more agents so that their combined effect is greater than their individual effects.

The term "antibacterial agent" as used herein refers to any substance, compound, a combination of substances, or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactamase" or "beta-lactamase enzyme" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to and includes compounds or materials used to facilitate administration of a compound, for example, to increase the solubility of the compound. Typical, non-limiting examples of solid carriers include starch, lactose, dicalcium phosphate, sucrose, and kaolin. Typical, non-limiting examples of liquid carriers include sterile water, saline, buffers, non-ionic surfactants, and edible oils. In addition, various adjuvants commonly used in the art may also be included. These and other such compounds are described in literature, e.g., in the Merck Index (Merck & Company, Rahway, N.J.). Considerations for inclusion of various components in pharmaceutical compositions are described, e.g., in Gilman et al. (Goodman and Gilman's: The Pharmacological Basis of Therapeutics, 8th Ed., Pergamon Press., 1990), which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" include humans, cats, dogs, horses, sheep, bovine cows, pigs, lambs, rats, mice and guinea pigs.

The term "cation" as used herein refers to all organic and inorganic positively charged ions. The term "organic cation" refers to all positively charged organic ions. Typical, non-limiting examples of organic cations include unsubstituted ammonium cations, alkyl substituted ammonium cations, cycloalkyl substituted ammonium cations, primary, secondary and tertiary amines, alkyl amines, cycloalkyl amines, aryl amines, N,N'-dibenzylethylenediamine and the like. The term "inorganic cation" refers to a positively charged metal ion. Typical, non-limiting examples of inorganic cations include Group I and Group II metal cations such as, for example, lithium, sodium, potassium, rubidium, cesium, beryllium, magnesium, calcium and the like.

In one general aspect, there are provided compounds of Formula (I):

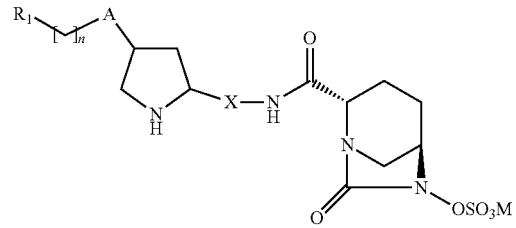

Formula (I)

or a stereoisomer or a pharmaceutically acceptable derivative thereof;

wherein:

X is selected from —CH₂—O— or —(C=O)—NH—;

A is heterocycloalkyl or heteroaryl optionally substituted with one or more substituents selected from $C_1$-$C_6$ alkyl, $NR_2R_3$, aryl, heteroaryl, cycloalkyl or heterocycloalkyl;

$R_1$ is selected from:
(a) hydrogen,
(b) $C_1$-$C_6$ alkyl optionally substituted with one or more substituents independently selected from $OR_2$, $NR_2R_3$, $SR_2$, halogen, CN, $COOR_2$, $CONR_2R_3$, $SR_2$, $CH_2OR_2$ or $CH_2NR_2R_3$, aryl, heteroaryl, cycloalkyl or heterocycloalkyl,
(c) halogen,
(d) CN,
(e) $CONR_2R_3$,
(f) $COOR_2$,
(g) CHO
(h) $NR_2R_3$,
(i) $NHCOOR_2$,
(j) $SR_2$,
(k) $SOR_2$,
(l) $SO_2R_2$,
(m) aryl,
(n) heteroaryl,
(o) cycloalkyl, or
(p) heterocycloalkyl;

$R_2$ and $R_3$ are each independently selected from:
(a) hydrogen,
(b) $C_1$-$C_6$ alkyl,
(c) cycloalkyl,
(d) heterocycloalkyl,
(e) aryl, or
(f) heteroaryl;

n is 0, 1, 2, 3 or 4;

M is hydrogen or a cation.

In some embodiments, there are provided compounds of Formula (I), wherein X is —CH₂—O—.

In some embodiments, there are provided compounds of Formula (I), wherein X is —(C=O)—NH—.

In some embodiments, there are provided compounds of Formula (I), wherein A is heterocycloalkyl.

In some embodiments, there are provided compounds of Formula (I), wherein A is heterocycloalkyl linked to pyrrolidine through "N" of heterocycloalkyl.

In some embodiments, there are provided compounds of Formula (I), wherein A is heteroaryl.

In some embodiments, there are provided compounds of Formula (I), wherein A is heteroaryl linked to pyrrolidine through "N" of heteroaryl.

Typical, non-limiting examples of compounds according to the invention include:

(2S,5R)—N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-tetrazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-tetrazol-1-yl)epyrrolidin-2-yl]methyloxy}-7-oxo-6-(sulfooxy)-1,6-diazabicyclo[3.2.1]octane-2-carboxamide;

(2S,5R)-N-{[(2R,4S)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-pyrrol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-pyrrol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(2-methyl-1H-1,3-imidazol-1-yl)pyrrolidin-2-yl]methyloxy }-7-oxo-6-(sulfooxy)-1,6-diazabicyclo[3.2.1]octane-2-carboxamide;

(2S,5R)-N-{[(2S,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-tetrazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-tetrazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2-methyl-1H-1,3-imidazol-1-yl)pyrrolidin-2-yl]methyloxy }-7-oxo-6-(sulfooxy)-1,6-diazabicyclo[3.2.1]octane-2-carboxamide;

(2S,5R)-N-{[(2S,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2-methyl-1H-1,3-imidazol-1-yl)pyrrolidin-2-yl]methyloxy }-7-oxo-6-(sulfooxy)-1,6-diazabicyclo[3.2.1]octane-2-carboxamide;

(2S,5R)-N-{[(2S,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-hydroxypiperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(4-hydroxypiperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-hydroxypiperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(4-hydroxypiperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1,3-Oxazeditin-3-yl)pyrroidin-2-yl]methyloxy}-7-oxo-6-(sulfooxy)-1,6-diazabicyclo[3.2.1]octane-2-carboxamide;

(2S,5R)-N-{[(2S,4S)-4-(1,3-Oxazeditin-3-yl)pyrroidin-2-yl]methyloxy}-7-oxo-6-(sulfooxy)-1,6-diazabicyclo[3.2.1]octane-2-carboxamide;

(2S,5R)-N-{[(2R,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1,3-Oxazeditin-3-yl)pyrroidin-2-yl]methyloxy}-7-oxo-6-(sulfooxy)-1,6-diazabicyclo[3.2.1]octane-2-carboxamide;

(2S,5R)-N-{[(2S,4R)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R, 4R)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1,3-oxazeditin-3-yl)pyrroidin-2-yl]methyloxy}7-oxo-6-(sulfooxy)-1,6-diazabicyclo[3.2.1]octane-2-carboxamide;

(2S,5R)-N-{[(2S,4S)-4-(1,3-oxazeditin-3-yl)pyrroidin-2-yl]methyloxy}7-oxo-6-(sulfooxy)-1,6-diazabicyclo[3.2.1]octane-2-carboxamide;

(2S,5R)-N-{[(2R,4R)-4-(1,3-oxazeditin-3-yl)pyrroidin-2-yl]methyloxy}7-oxo-6-(sulfooxy)-1,6-diazabicyclo[3.2.1]octane-2-carboxamide;

(2S,5R)-N-{[(2R,4S)-4-(1,3-oxazeditin-3-yl)pyrroidin-2-yl]methyloxy}7-oxo-6-(sulfooxy)-1,6-diazabicyclo[3.2.1]octane-2-carboxamide;

(2S,5R)-N-{[(2R,4R)-4-(1,3-thiazolidin-3-yl)pyrrolidin-2-yl]methyloxy}7-oxo-6-(sulfooxy)-1,6-diazabicyclo[3.2.1]octane-2-carboxamide;

(2S,5R)-N-{[(2S,4S)-4-(1,3-thiazolidin-3-yl)pyrrolidin-2-yl]methyloxy}7-oxo-6-(sulfooxy)-1,6-diazabicyclo[3.2.1]octane-2-carboxamide;

(2S,5R)-N-{[(2R,4R)-4-(1,3-thiazolidin-3-yl)pyrrolidin-2-yl]methyloxy}7-oxo-6-(sulfooxy)-1,6-diazabicyclo[3.2.1]octane-2-carboxamide;

(2S,5R)-N-{[(2R,4S)-4-(1,3-thiazolidin-3-yl)pyrrolidin-2-yl]methyloxy}7-oxo-6-(sulfooxy)-1,6-diazabicyclo[3.2.1]octane-2-carboxamide;

(2S,5R)-N-{[(2R,4S)-4-[4-({[(2S)-1-hydroxypropan-2-yl]amino}methyl)piperidin-l-yl] pyrrolidin-2-yl]methoxy}-7-oxo-6-(sulfooxy)-1,6-diazabicyclo[3.2.1]octane-2-carboxamide;

(2S,5R)-N-{[(2S,4S)-4-(1H-tetrazol-1-yl)pyrrolidin-2-yl]carbonyl}-7-oxo-6-(sulfooxy)--1,6-diazabicyclo[3.2.1]octane-2-carbohydrazide;

(2S,5R)-N-{[(2S,4S)-4-(2H-tetrazol-2-yl)pyrrolidin-2-yl]carbonyl}-7-oxo-6-(sulfooxy)-1,6-diazabicyclo[3.2.1]octane-2-carbohydrazide;

(2S,5R)-N-{[(2S,4S)-4-(5 -methyl-2H-tetrazol-2-yl)pyrrolidin-2-yl]carbonyl}-7-oxo-6-(sulfooxy)-1,6-diazabicyclo[3.2.1]octane-2-carbohydrazide;

(2R,5R)-N-{[(2S,4S)-4-(2H-1,2,3-triazol-2-yl)pyrrolidin-2-yl]carbonyl}-7-oxo-6-(sulfooxy)--1,6-diazabicyclo[3.2.1]octane-2-carbohydrazide; (2R,5R)-N-{[(2S,4S)-4-(1H-1,2,3-triazol-1-yl)pyrrolidin-2-yl]carbonyl}-7-oxo-6-(sulfooxy)-1,6-diazabicyclo[3.2.1]octane-2-carbohydrazide; (2R,5R)-7-oxo-6-(sulfooxy)-N-{[(2S,4S)-4-(1H-1,2,4-triazol-1-yl)pyrrolidin-2-yl]carbonyl}-1,6-diazabicyclo[3.2.1]octane-2-carbohydrazide;

(2S,5R)-N'-{[(2S,4S)-4-(1H-imidazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2RS,4S)-4-(1H-imidazol-1-yl) pyrrolidin-2-yl]carbonyl}-7-oxo-6-(sulfooxy)-1,6-diazabicyclo[3.2.1]octane-2-carbohydrazide;

(2S,5R)-N-{[(2S,4R)-4-(1H-pyrazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2SR, 4S)-4-(1H-pyrazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2S,4R)-4-(1H-imidazol-1-yl)pyrrolidin-2-yl]carbonyl}-7-oxo-6-(sulfooxy)-1,6-diazabicyclo[3.2.1]octane-2-carbohydrazide;

(2S ,5R)-N-{[(2R,4S)-4-(1H-imidazol-1-yl)pyrrolidin-2-yl]carbonyl}-7-oxo-6-(sulfooxy)-1,6-diazabicyclo[3.2.1]octane-2-carboxhydrazide;

or a stereoisomer or a pharmaceutically acceptable derivative thereof.

In some other embodiments, typical, non-limiting examples of compounds according to the invention include:

Sodium salt of (2S,5R)-N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(2H-1,2,3-triazol-2-yl)pyrrolidin-2-yl]methyloxy}-7-oxo-6-(sulfooxy)-1,6-diazabicyclo[3.2. 1] octane-2-carboxamide;

Sodium salt of (2S,5R)-N-{[(2S,4S)-4-(1H-1,2,3-triazol-1-yl)pyrrolidin-2-yl]methyloxy}-7-oxo-6-(sulfooxy)-1,6-diazabicyclo[3.2. 1] octane-2-carboxamide;

Sodium salt of (2S,5R)-N-{[(2R,4S)-4-(1H-1,3-imidazol-1-yl)pyrrolidin-2-yl]methyloxy}-7-oxo-6-(sulfooxy)-1,6-diazabicyclo[3.2. 1] octane-2-carboxamide;

Sodium salt of (2S,5R)-N-{[(2S,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-1,2,4-triazol-1-yl)pyrrolidin-2-yl]methyloxy}-7-oxo-6-(sulfooxy)-1,6-diazabicyclo[3.2.1] octane-2-carboxamide;

Sodium salt of (2S,5R)-N-{[(2S,4S)-4-(1H-1,3-imidazol-1-yl)pyrrolidin-2-yl]methyloxy}-7-oxo-6-(sulfooxy)-1,6-diazabicyclo[3.2.1] octane-2-carboxamide;

Sodium salt of (2S,5R)-N-{[(2R,4S)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(2H-1,2,3-triazol-2-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4S)-4-(1H-1,2,3-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4S)-4-(1H-1,2,4-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-pyrrol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-pyrrol-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2S,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-benzimidazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4R)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(2H-1,2,3-triazol-2-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4R)-4-(1H-1,2,3-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4R)-4-(1H-1,2,4-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2R,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-pyrrole-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-pyrrole-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2R,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-benzimidazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2S,4R)-4-(1H-pyrrole-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2H-1,2,3-triazol-2-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2S,4R)-4-(1H-1,2,3-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2S,4R)-4-(1H-1,2,4-triazol-1-yl)pyrrolidin-2-yl]methyloxy}7-oxo-6-(sulfooxy)-1,6-diazabicyclo[3.2.1]octane-2-carboxamide;

Sodium salt of (2S,5R)-N-{[(2S,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2R,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2S,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-benzimidazol-1-yl)pyrrolidin-2-yl]methyloxy}7-oxo-6-(sulfooxy)-1,6-diazabicyclo[3.2.1]octane-2-carboxamide;

Trifluoro acetic acid salt of (2S,5R)-N-{[(2S,4R)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(4-hydroxypiperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(4-hydroxypiperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(4-hydroxypiperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(4-hydroxypiperidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(4-methylpiperazin--yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(4-methylpiperazin--yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(4-methylpiperazin--yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(pyrrolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(imidazolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-[4-({[(2S)-1-hydroxypropan-2-yl]amino}methyl)piperidin-1-yl]pyrrolidin-2-yl]methoxy}-7-oxo-6-(sulfooxy)-1,6-diazabicyclo[3.2.1]octane-2-carboxamide;

Sodium salt of (2S,5R)-N-{[(2S,4S)-4-(1H-tetrazol-1-yl)pyrrolidin-2-yl]carbonyl}-7-oxo-6-(sulfooxy)--1,6-diazabicyclo[3.2.1]octane-2-carbohydrazide;

Sodium salt of (2S,5R)-N'-{[(2S,4S)-4-(2H-tetrazol-2-yl)pyrrolidin-2-yl]carbonyl}-7-oxo-6-(sulfooxy)-1,6-diazabicyclo[3.2.1]octane-2-carbohydrazide;

Sodium salt of (2S,5R)-N'{[(2S,4S)-4-(5-methyl-2H-tetrazol-2-yl)pyrrolidin-2-yl]carbonyl}-7-oxo -6-(sulfooxy)-1,6-diazabicyclo[3.2.1]octane-2-carbohydrazide;

Sodium salt of (2R,5R)-N'-{[(2S,4S)-4-(2H-1,2,3-triazol-2-yl)pyrrolidin-2-yl]carbonyl}-7-oxo-6-(sulfooxy)- -1,6-diazabicyclo[3.2.1]octane-2-carbohydrazide;

Sodium salt of (2R,5R)-N'-{[(2S,4S)-4-(1H-1,2,3-triazol-1-yl)pyrrolidin-2-yl]carbonyl}-7-oxo-6-(sulfooxy)-1,6-diazabicyclo[3.2.1]octane-2-carbohydrazide;

Sodium salt of (2R,5R)-7-oxo-6-(sulfooxy)-{[(2S,4S)-4-(1H-1,2,4-triazol-1-yl)pyrrolidin-2-yl]carbonyl}-1,6-diazabicyclo[3.2.1]octane-2-carbohydrazide;

Sodium salt of (2S,5R)-N'-{[(2S,4S)-4-(1H-imidazol-1-yl)pyrrolidin-2-yl]carbonyl}-7-oxo-6-(sulfooxy)-1,6-diazabicyclo[3.2.1]octane-2-carbohydrazide;

Sodium salt of (2S,5R)-N'-{[(2RS,4S)-4-(1H-imidazol-1-yl) pyrrolidin-2-yl]carbonyl}-7-oxo-6-(sulfooxy)-1,6-diazabicyclo[3.2.1]octane-2-carbohydrazide;

Sodium salt of (2S,5R)-N-{[(2S,4R)-4-(1H-pyrazol-1-yl)pyrrolidin-2-yl]carbonyl}-7-oxo-6-(sulfooxy)-1,6-diazabicyclo[3.2.1]octane-2-carbohydrazide;

Sodium salt of (2S,5R)-N'-{[(2SR, 4S)-4-(1H-pyrazol-1-yl)pyrrolidin-2-yl]carbonyl}-7-oxo-6-(sulfooxy)-1,6-diazabicyclo[3.2.1]octane-2-carbohydrazide;

Trifluoro acetic acid salt of (2S,5R)-N'-{[(2S,4R)-4-(1H-imidazol-1-yl)pyrrolidin-2-yl]carbonyl}-7-oxo-6-(sulfooxy)-1,6-diazabicyclo[3.2.1]octane-2-carbohydrazide;

Trifluoro acetic acid salt of (2S,5R)-N-{[(2R,4S)-4-(1H-imidazol-1-yl)pyrrolidin-2-yl]carbonyl}-7-oxo-6-(sulfooxy)-1,6-diazabicyclo[3.2.1]octane-2-carboxhydrazide;

or a stereoisomer thereof.

In general, the compounds of the invention can be prepared according to the general procedures given in Scheme 1. A person of skills in the art would appreciate that the described method can be varied or optimized further to provide the desired and related compounds. In the following procedures all variables are as defined above.

Typically, 4-hydroxy-pyrrolidine-2-carboxylic acid (II) is reacted with a suitable carboxyl activating agent in presence of a suitable solvent at a temperature of about 0-30° C. for about 1-24hours to obtain a compound of Formula (III). In some embodiments, compound of Formula (II) is reacted with thionyl chloride in presence of methanol at room temperature for about 16 hours to obtain a compound of Formula (III). The so obtained compound of Formula (III) is treated with di-tert-butyl dicarbonate in presence of a suitable base such as triethylamine to obtain a compound of Formula (IV). The hydroxyl group of compound of Formula (IV) is protected with a suitable reagent to obtain a compound of Formula (V), wherein R' is the suitable activating group which can be easily replaceable. The compound of Formula (IV) is treated with a suitable reagent selected from methanesulfonyl chloride, toluenesufonyl chloride, nosyl chloride or trifluoromethanesulfonic anhydride in presence of a suitable base such as N-ethyldiisopropyl amine, triethylamine, dimethylaminopyridine or a mixture thereof to obtain a compound of Formula (V).

The compound of Formula (V) is treated with a compound of Formula (Y) in presence of a base and suitable solvent at a temperature of about 40-100° C. for about 1-24hours to obtain a compound of Formula (VI). In some embodiments, a compound of Formula (V) is treated with a compound of Formula (Y) in presence of dimethylformamide and suitable base such as potassium carbonate or cesium carbonate at about 25-80° C. for about 1-16 hours to obtain a compound of Formula (VI).

The compound of Formula (VI) is treated with suitable reagent(s) to obtain a compound of Formula (VII), wherein X is —CH$_2$-O or —(C=O)—NH—. In some embodiments, the compound of Formula (VI) is treated with suitable reagent(s) to obtain compound of Formula (VII) wherein X—CH$_2$-0. This conversion is effected in two steps. First, compound of Formula (VI) is reduced with a suitable reducing agent in presence of a suitable solvent at temperatures ranging from −15° C. to 60° C. for about 1 to 24hours to obtain a primary alcoholic compound. Typical, non-limiting example of reducing agents includes lithium aluminium hydride. Typical non-limiting examples of suitable solvents include tetrahydrofuran, 1,4-dioxane, toluene or mixtures thereof. The primary alcoholic compound so obtained is further converted to a phthalimido intermediate in presence of triphenyl phosphine and N-hydroxy phthalimide at temperatures ranging from −15° C. to 60° C. for about 1 to 24 hours. This intermediate is then treated with hydrazine hydrate at temperatures ranging from −15° C. to 60° C. for about 1 to 24hours to obtain compound of formula (VII).

In some embodiments, the compound of Formula (VI) is converted to compound of Formula (VII) wherein X is —(C=O)—NH—. The compound of Formula (VI) is treated with hydrazine hydrate at temperatures ranging from −15° C. to 60° C. for about 1 to 24hours to obtain a compound of Formula (VII).

The so obtained compound of Formula (VII) is treated with sodium salt of (2S,5R)-6-benzyloxy-7-oxo-1,6-diazabicyclo[3.2.1]octane-2-carboxylic acid (VIII), (prepared as per the procedure disclosed in International Patent Application No. PCT/IB2013/059264) in presence of a suitable coupling agent and a suitable solvent at a temperature ranging from about −15° C. to about 60° C. for about 1 to about 24hours to obtain a compound of Formula (IX). Typical, non-limiting examples of suitable coupling agents include dicyclohexylcarbodiimide (DCC), 1-ethyl-3-(3-dimethylaminopropyl) carbodiimide hydrochloride (EDC.HCl), diisopropylcarbodiimide (DIC), 1-hydroxybenzotriazole (HOBt), N-hydroxysuccinimide (HOSu), 1-Hydroxy-7-azabenzotriazolo (HOAt), (1-[Bis(dimethylamino)methylene]-1H-1,2,3-triazolo[4,5-b]pyridinium-3-oxidhexafluoro phosphate) (HATU), PyB OP, PyBrop, HAMTU, 2-(5 -Norborene-2,3-dicarboximido)-1,1,3,3-tetramethyluronium tetrafluoroborate (TNTU), 2-(2-Pyridon-1-y1)-1,1,3,3-tetramethyluronium tetrafluoroborate (TPTU) and the like. Typical, non-limiting examples of suitable solvents include N,N-dimethylformamide, N,N-dimethylacetamide, 1,4-dioxane, chloroform, dichloromethane, tetrahydrofuran, acetonitrile, water and their appropriate combinations and the like.

The compound of Formula (IX) is debenzylated by carrying out hydrogenolysis in presence of hydrogen, transition metal catalyst and a suitable solvent at a temperature ranging from about 10° C. to about 60° C. for about 1 hour to about 14hour to provide a compound of Formula (X). Typical, non-limiting examples of hydrogen source include hydrogen gas, ammonium formate, cyclohexene, lithium—liquid ammonia, ammonia—tert-butanol, sodium—liquid ammonia—tert-butanol, triethyl silyl hydride and the like. Typical, non-limiting examples of transition metal catalyst include 5% palladium on carbon, 10% palladium on carbon, 20% palladium hydroxide on carbon, Raney-Nickel and the like. Typical, non-limiting examples of suitable solvent include methanol, ethanol, dichloromethane, N,N dimethylformamide, ethyl acetate, tetrahydrofuran or a mixture thereof.

The compound of Formula (X) is sulfonated by reacting with suitable sulfonating reagent in a suitable solvent such as pyridine, dichloromethane or N,N-dimethylformamide, at a temperature ranging from about 0° C. to about 80° C. for about 1 hour to about 24hour. Typical non-limiting examples of suitable sulfonating reagent include sulfur trioxide pyridine complex, sulfur trioxide trimethylamine complex, sulfur trioxide triethylamine complex, sulfur trioxide N,N-dimethylaniline complex, sulfur trioxide 2-methylpyridine complex, sulfur trioxide dioxane complex, sulfur trioxide thioxane complex, sulfur trioxide dimethyl sulfide complex, sulfur trioxide dimethylsulfoxide complex, sulfur trioxide N,N-dimethylformamide complex and the like. The obtained sulfonated compound was converted to corresponding tetrabutylammonium salt of Formula (XI). In some embodiments, the sulfonated compound is treated with tetrabutylammonium sulfate (TBAS) to obtain tetrabutylammonium salt of sulfonic acid compound of Formula (XI).

The compound according to the invention is then isolated as zwitterion, by removing the protecting groups of compound of Formula (XI). The compound of Formula (XI) is reacted with suitable deprotecting agent such as trifluoroacetic acid in presence of a suitable solvent such as dichloromethane, chloroform or acetonitrile, at a temperature ranging from about −15° C. to about 40° C. for about 0.5 hour to about 14hour to obtain a compound of Formula (I), wherein M is H.

Scheme 1

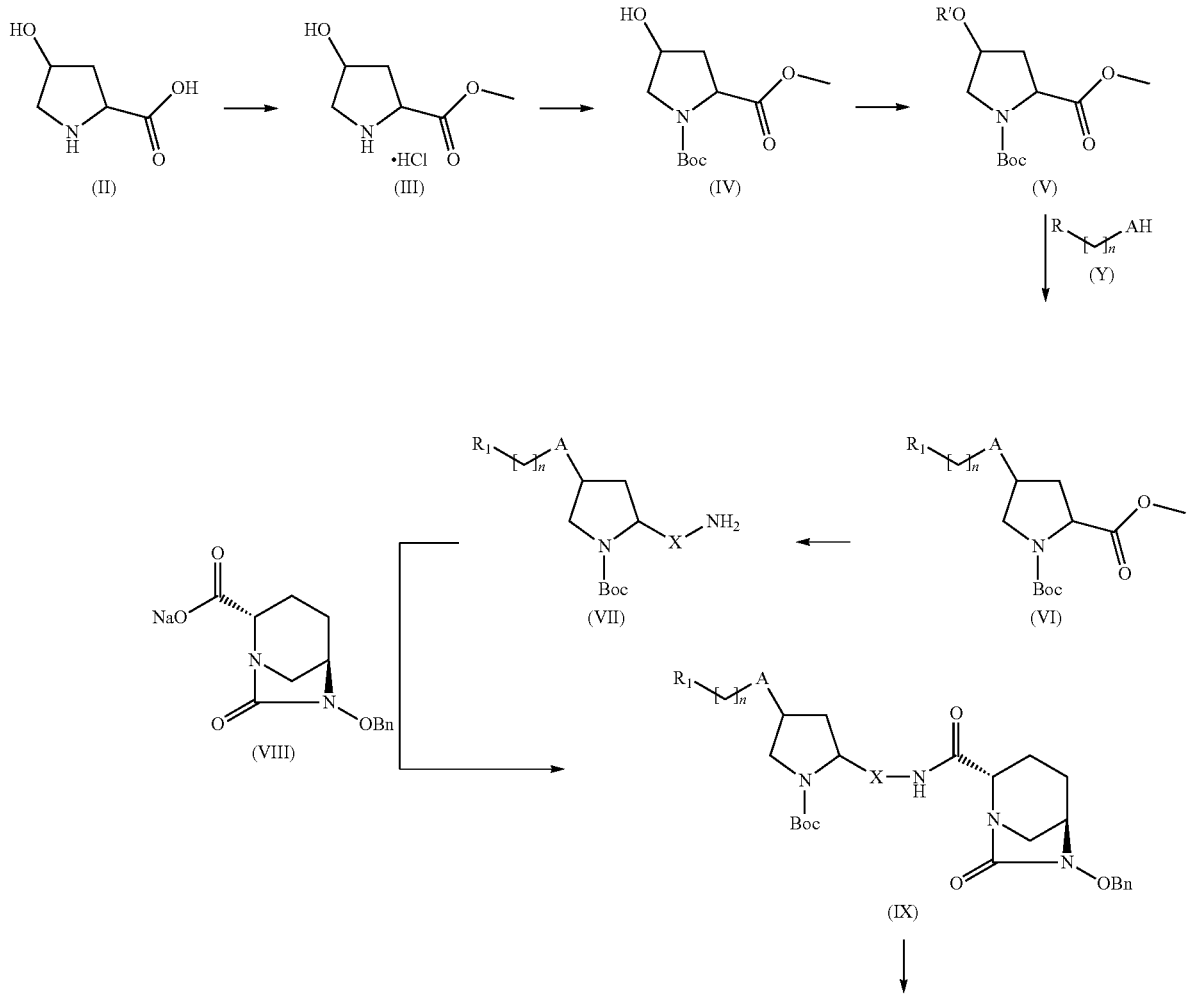

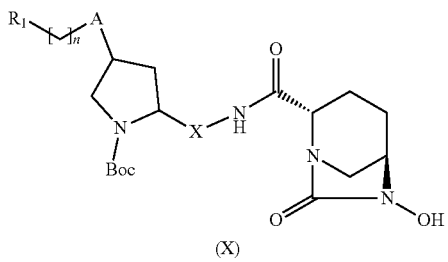
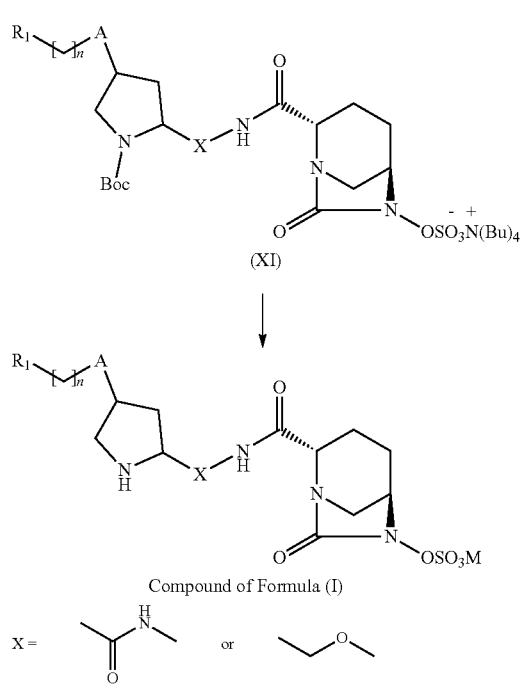

Compound of Formula (I)

The compound of Formula (XI) may also be converted to compound of Formula (I), wherein M is a cation. In some embodiments, compound of Formula (VI) was dissolved in suitable solvent such as 10% tetrahydrofuran: water mixture and was passed through the column packed with Dowex 50WX8 200 Na+ resin or passing through Indion 225 Na resin to provide sodium salt of compound of Formula (I). In some embodiments, compound of Formula (XI) was dissolved in suitable solvent such as acetone, tetrahydrofuran, ethanol, isopropanol or acetonitrile and thereby treating with sodium ethylhexanoate or potassium ethylhexanoate to provide sodium or potassium salt of compound of Formula (I).

In some embodiments, there are provided pharmaceutical compositions comprising a compound of Formula (I) or a stereoisomer or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) a compound of Formula (I) or a stereoisomer or a pharmaceutically acceptable derivative thereof, (b) at least one beta-lacatamse inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject a compound of Formula (I) or a stereoisomer or a pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, the compositions and methods according to the invention use compounds of Formula (I), or a stereoisomer or a pharmaceutically acceptable derivative thereof in combination with at least one antibacterial agent or a pharmaceutically acceptable derivative thereof. A wide variety of antibacterial agents can be used. Typical, non-limiting examples of antibacterial agents include one or more of antibacterial compounds generally classified as aminoglycosides, ansamycins, carbacephems, cephalosporins, cephamycins, lincosamides, lipopeptides, macrolides, monobactams, nitrofurans, penicillins, polypeptides, quinolones, sulfonamides, tetracyclines, oxazolidinone and the like. Typical, non-limiting examples of aminoglycoside antibacterial agents include amikacin, gentamicin, kanamycin, neomycin, netilmicin, tobramycin, paromomycin, arbekacin, streptomycin, apramycin and the like. Typical, non-limiting examples of ansamycin antibacterial agents include geldanamycin, herbimycin and the like. Typical, non-limiting examples of carbacephem antibacterial agents include loracarbef and the like. Typical, non-limiting examples of carbapenem antibacterial agents include ertapenem, doripenem, imipenem, meropenem and the like.

Typical, non-limiting examples of cephalosporin and cephamycin antibacterial agents include cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cephamycin, cefoxitin, cefotetan, cefmetazole, carbacephem, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, ceftiolene, ceftizoxime, cxacephem, cefepime, cefozopran, cefpirome, cefquinome, ceftobiprole, ceftiofur, cefquinome, cefovecin, ceftolozane, ceftaroline, ceftobiprole and the like Typical, non-limiting examples of lincosamide antibacterial agents include clindamycin, lincomycin and the like. Typical, non-limiting examples of macrolide antibacterial agents include azithromycin, clarithromycin, dirithromycin, erythromycin, roxithromycin, troleandomycin, telithromycin, spectinomycin, solithromycin and the like. Typical, non-limiting examples of monobactam antibacterial agents include aztreonam and the like. Typical, non-limiting examples of nitrofuran antibacterial agents include furazolidone, nitrofurantoin and the like. Typical, non-limiting examples of penicillin antibacterial agents include amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin and the like. Typical, non-limiting examples of polypeptide antibacterial agents include bacitracin, colistin, polymyxin B and the like.

Typical, non-limiting examples of quinolone antibacterial agents include ciprofloxacin, enoxacin, gatifloxacin, levofloxacin, lomefloxacin, moxifloxacin, nalidixic acid, levonadifloxacin, norfloxacin, ofloxacin, trovafloxacin, grepafloxacin, sparfloxacin, temafloxacin and the like. Typical, non-limiting examples of sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and the like. Typical, non-limiting examples of tetracycline antibacterial agents include demeclocycline, doxycycline, minocycline, oxytetracycline, tetracycline, tigecycline and the like. Typical, non-limiting examples of oxazolidinone antibacterial agents include tedizolid, linezolid, ranbezolid, torezolid, radezolid and the like.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

In some embodiments, pharmaceutical compositions according to the present invention are administered orally or parenterally.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for oral or parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture to a subject using any suitable route of administration. Alternatively, pharmaceutical compositions according to the invention may also be formulated into a dosage form wherein one or more ingredients (active or inactive ingredients) are present as separate components. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

In some embodiments, pharmaceutical compositions according to the invention are formulated into a dosage form such that the compound of Formula (I) or a stereoisomer or a pharmaceutically acceptable derivative thereof, and the antibacterial agent or a pharmaceutically acceptable derivative thereof, are present in the composition as admixture or as separate components. In some other embodiments, pharmaceutical compositions according to the invention are formulated into a dosage form such that the compound of Formula (I) or a stereoisomer or a pharmaceutically acceptable derivative thereof, and the antibacterial agent or a pharmaceutically acceptable derivative thereof, are present in the composition as separate components.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) or are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, compositions and methods according to the invention are also effective in preventing or treating bacterial infections that are caused by bacteria producing one or more beta-lactamase enzymes. In some embodiments, there are provided methods of inhibiting beta-lactamase enzymes, wherein said methods comprise administering a pharmaceutically effective amount of a compound of Formula (I), or a stereoisomer or a pharmaceutically acceptable derivative thereof. In some other embodiments, there are provided methods of inhibiting beta-lactamase enzymes, wherein said methods comprise administering a pharmaceutically effective amount of a pharmaceutical composition comprising a compound of Formula (I), or a stereoisomer or a pharmaceutically acceptable derivative thereof.

In general, the compounds of Formula (I), or a stereoisomer or pharmaceutically acceptable salt thereof according to invention are also useful in increasing antibacterial effectiveness of antibacterial agent in a subject. The antibacterial effectiveness of one or more antibacterial agents may increased, for example, by co-administering said antibacterial agent or a pharmaceutically acceptable derivative thereof with a pharmaceutically effective amount of a compound of Formula (I), or a stereoisomer or a pharmaceutically acceptable salt thereof according to the invention. In some embodiments, there is provided a method for increasing antibacterial effectiveness of the antibacterial agent in a subject, said method comprising co-administering said antibacterial agent or a pharmaceutically acceptable derivative thereof with a of a compound of Formula (I), or a stereoisomer or a pharmaceutically acceptable derivative thereof.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

(2S,5R)-N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide

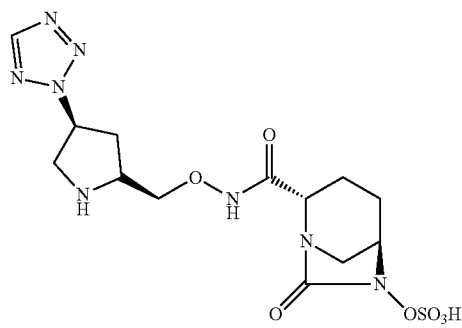

Step 1: Synthesis of methyl (2S,4R)-4-hydroxy-pyrrolidine-2-carboxylate hydrochloride: To a stirred solution of (2S,4R)-4-hydroxy-pyrrolidine-2-carboxylic acid (100.0 g, 0.76 mol) in methanol (1 L) at 0° C. was added thionyl chloride (66.0 ml, 0.91 M) using addition funnel over 30 minutes. The reaction mixture was then slowly allowed to warm to room temperature and stirred for 16 hours. The solvent was then evaporated under reduced pressure. To the obtained white residue, hexane (1 L) was added, stirred well and filtered under suction. The residue was washed with additional hexane (1 L). The white residue obtained was then transferred to 1 L round bottomed flask and dried under reduced pressure (2 mm Hg) for 2 hours to obtain 135 g of titled compound as a white solid in 98% yield.

Analysis:

Mass: 146 (M+1); for Molecular weight: 145.1 and Molecular formula: $C_6H_{11}NO_3$ $^1$H NMR (CDCl$_3$, 400 MHz): δ 4.62×4.58 (m, 2H), 3.85 (s, 3H), 3.45 (dd, 1H, J=3.6, 12.0 Hz), 3.34×3.29 (m, 1H), 2.44×2.38 (m, 1H), 2.24-2.16 (m, 1H);

Step 2: Synthesis of (2S,4R)-1-tert-butyl-2-methyl-4-hydroxypyrrolidine-1,2-dicarboxylate: To a stirred solution of methyl (2S,4R)-4-hydroxy-pyrrolidine-2-carboxylate hydrochloride (135.0 g, 0.74mol) in dichloromethane (1.3 L) at 0° C., was slowly added triethylamine (207 ml, 1.49 mol) using addition funnel over 30 minutes. After this Boc anhydride (179.0 g, 0.81 mol) was added to the reaction mixture using addition funnel over 30 minute. The reaction mixture was then allowed to warm to room temperature and stirred further for 16 hours. The reaction mixture was then transferred to 3 L separating funnel and washed with 10% potassium hydrogen sulfate (2×1 L), 5% sodium hydrogen carbonate (2×1 L) and then with water (2×2 L). The organic layer was then dried over sodium sulfate, filtered and solvent was evaporated under reduced pressure to obtain 166 g of the titled compound as light yellow oil in 91% yield.

Analysis:

Mass: 246 (M+1); for Molecular weight: 245.2 and Molecular formula: $C_{11}H_{19}NO_5$ $^1$H NMR (CDCl$_3$, 400 MHz): δ 4.50-4.35 (m, 2H), 3.68-3.40 (m, 2H), 2.30 -2.27 (m, 1H), 2.09-2.02 (m, 1H), δ1.45 (s, 9H);

Step 3: Synthesis of (3R,5S)-1-(tert-butoxycarbonyl)-5-(methoxycarbonyl)pyrrolidin-3-yl-4-(4-nitrobenzenesulfonate): To a stirred solution of (2S,4R)-1-tent-butyl 2-methyl-4-hydroxy pyrrolidine-1,2-dicarboxylate (100.0 g, 0.40 mol) in dichloromethane (1 L) at 0° C. was added triethylamine (170.0 ml, 1.22 mol) over 10 minute using addition funnel, followed by dimethylaminopyridine (3.27 g, 0.02 M). Nosyl chloride (108.7 g, 0.48 mol) was slowly added to the reaction mixture over 30 minute. The reaction was highly exothermic. The reaction mixture was then allowed to warm to room temperature and stirred for 16 hours. The reaction mixture was then washed with 5% potassium hydrogen sulfate (2×1 L), 10% sodium hydrogen carbonate (2×1 L) and then with water (2×1 L). The organic later was dried over sodium sulfate, filtered and solvent was evaporated under reduced pressure to obtain thick oil. Diethyl ether (500 ml) was added to the thick oil, stirred well and then evaporated under reduced pressure to obtain white solid. To the obtained white residue, hexane (1 L) was added and the mixture was stirred for 30 minutes. The mixture was then filtered under suction and the residue washed several times with hexane (3×200 ml). The obtained white residue was transferred to 1 L round bottom flask and dried under reduced pressure (4 mm Hg) to obtain 143 g of (3R,5S)-1-

(tert-butoxycarbonyl)-5-(methoxycarbonyl) pyrrolidin-3-yl-4-nitrobenzenesulfonate as white powder in 81% yield.

Analysis:

Mass: 431 (M+1); for Molecular weight: 430.4 and Molecular formula: $C_{17}H_{22}N_2O_9S$ $^1$H NMR (CDCl$_3$, 400 MHz): δ 8.42 (d, 1H, J=8.4Hz), 8.11 (d, 1H, J=8.4Hz), 5.18 (bs, 1H), 4.41-4.34(m, 1H), 3.73(s, 3H), 3.70-3.60 (m, 2H), 2.62-2.42 (m, 1H), 2.26-2.20 (m, 1H), 1.43(s, 9H).

Step 4: Synthesis of (2S,4S)-1-tert-butyl-2-methyl 4-(2H-tetrazol-2-yl)pyrrolidine-1,2-dicarboxylate and (2S,4S)-1-tert-butyl 2-methyl 4-(1H-tetrazol-1-yl)pyrrolidine-1,2-dicarboxylate: To a stirred solution of compound (3R,5S)-1-(tert-butoxycarbonyl)-5-(methoxycarbonyl) pyrrolidin-3-yl-(4-nitrobenzenesulfonate) (20.0 g, 0.04 mol) in dimethylformamide (150 ml) was added potassium carbonate (12.8 g, 0.09 mol) and tetrazole (3.58 g, 0.05 mol). The reaction mixture was heated at 80° C. for 16 hours. The solvent was evaporated under reduced pressure. The residue was dissolved in ethyl acetate (150 ml) and the solution was washed with water (2×100 ml). The organic layer was then collected, dried over sodium sulfate, filtered and the solvent was evaporated under reduced pressure. The residue obtained was then purified using column chromatography over silica gel (60-120 mesh) using a gradient of 0:100-80:20 (Ethyl acetate: Hexane). The combined fractions were evaporated to obtain (2S,4S)-1-tert-butyl 2-methyl 4-(2H-tetrazol-2-yl)pyrrolidine-1,2-dicarboxylate as light yellow oil (8.1 g, 59%). Further elution and evaporation of the solvent from the combined fractions gave the (2S,4S)-1-tert-butyl 2-methyl 4-(1H-tetrazol-1-yl)pyrrolidine-1,2-dicarboxylate as colorless oil (3.7 g, 25%).

Analysis for (2S,4S)-1-tert-butyl 2-methyl 4-(2H-tetrazol-2-yl)pyrrolidine-1,2-dicarboxylate:

Mass: 298 (M+1); for molecular weight: 297.3 and Molecular formula: $C_{12}H_{19}N_5O_4$ $^1$H NMR (CDCl$_3$, 400 MHz): δ 8.52 (s, 1H), 5.37-5.30 (m, 1H), 4.53×4.49 (m, 1H), 4.22-4.11 (m, 2H), 3.69 (s, 3H), 3.02-2.95 (m, 2H), 1.42 (s, 9H);

Analysis for (2S,4S)-1-tert-butyl 2-methyl 4-(1H-tetrazol-1-yl)pyrrolidine-1,2-dicarboxylate:

Mass: 298 (M+1); for molecular weight: 297.3 and Molecular formula: $C_{12}H_{19}N_5O_4$ $^1$H NMR (CDCl$_3$, 400 MHz): δ 8.82 (s, 1H), 5.25 (bs, 1H), 4.58-4.42 (m, 1H), 4.16 (dd, 1H, J=6.4, 12.0 Hz), 4.10-3.82 (m, 1H), 3.67 (s, 3H), 3.05-2.90 (m, 1H), 2.75-2.55 (m, 1H), 1.44(s, 9H).

Step 5: Synthesis of (2S,4S)-tert-butyl-2-(hydroxymethyl)-4-(2H-tetrazol-2-yl)pyrrolidine-1-carboxylate: To a stirred solution of lithium aluminium hydride (0.83 g, 0.022 mol) in tetrahydrofuran (80 ml) at 0° C. was added (dropwise) a solution of compound (2S,4S)-1-tert-butyl 2-methyl 4-(2H-tetrazol-2-yl)pyrrolidine-1,2-dicarboxylate (7.0 g, 0.022 M) in tetrahydrofuran (50 ml). The resulting mixture was stirred for 2 hours at the same temperature. Saturated aqueous solution of sodium sulfate was then slowly added to the reaction mixture and stirred until the entire grey solid was turned in to white solid. The reaction mixture was then filtered through celite, the filtrate was collected and solvent was evaporated under reduced pressure. Ethyl acetate (150 ml) was added to the residue and the solution was transferred to a separating funnel and washed with water (2×100 ml). The organic layer was collected, dried over sodium sulfate, filtered and the solvent was evaporated under reduced pressure to obtain 4.2 g of the titled compound as colorless oil in 66% yield.

Step 6: Synthesis of tert-butyl-2-{[(2S,4S)-4-(2H-tetrazol-2-yl)pyrrolidin-2-yl]methyloxy}-1H-isoindole-1,3(2H)-dione-1-carboxylate: To a stirred solution of (2S,4S)-tert-butyl 2-(hydroxymethyl)-4-(2H-tetrazol-2-yl)pyrrolidine-1-carboxylate (3.64 g, 0.013 mol) in tetrahydrofuran (50 ml) was added triphenyl phosphine (3.90 g, 0.014 mol), N-hydroxy phthalamide (2.42 g, 0.014 mol) and diisopropyl azodicarboxylate (2.95 ml, 0.014 mol). The resulting mixture was stirred at room temperature for 16 hours. Solvent was evaporated under reduced pressure and diisopropyl ether (150 ml) was added to the residue and stirred at room temperature for 1 hour. The triphenyl phosphine oxide which was precipitated out was filtered off, the filtrate was collected and solvent evaporated under reduced pressure. The residue obtained was purified by column chromatography over silica gel (60-120 mesh) using a v/v gradient of 0:100-50:50 (Ethyl Acetate:Hexane). The solvent from the combined fractions was evaporated under reduced pressure to obtain 4.54 g of the titled compound as colorless oil in 81% yield.

Analysis:

Mass: 415 (M+1); for Molecular weight: 414.4 and Molecular formula: $C_{19}H_{22}N_6O_5$ $^1$H NMR (CDCl$_3$, 400 MHz): δ 8.56 (s, 1H), 7.82-7.72 (m, 4H), 5.50-5.40 (m, 1H), 4.55 (bs, 1H), 4.40-4.20 (m, 3H), 3.98 (dd, 1H, J=6.4, 12.0 Hz), 3.18-2.95 (m, 2H), 1.43(s, 9H).

Step 7: Synthesis of tert-butyl (2S,4S)-2-[(aminooxy)methyl]-4-(2H-tetrazol-2-yl)pyrrolidine-1-carboxylate: To a stirred solution of compound obtained in Step 6 (4.54 g, 0.011 M) in dichloromethane (50 ml) was added hydrazine hydrate (0.807 mL, 0.016 M) and the reaction mixture was stirred at room temperature for 2 hours. The white solid precipitated out in the reaction mixture was filtered off, the filtrate was collected and solvent was removed under reduced pressure to give the titled hydroxylamine compound, which was used in next reaction without further purification.

Step 8: Synthesis of (2S,5R)-N-{[1-tert-butoxycarbonyl (2S,4S)-4-(2H-tetrazol-2-yl)pyrrolidin-2-yl]methyloxy}-6-benzyloxy-7-oxo-1,6-diazabicyclo[3.2.1]octane-2-carboxamide: To a stirred solution of sodium salt of (2S,5R)-6-benzyloxy-7-oxo-1,6-diaza-bicyclo[3.2.1] octane-2-carboxylic acid, (prepared as per the procedure disclosed in International Patent Application No. PCT/IB2013/059264) (3.57 g, 0.011 mol) in dimethylformamide (100 ml) were successively added N-methyl morpholine (3.77 mL, 0.032 mol), EDC. HCl (3.13 g, 0.016 mol), HOBt (1.66 g, 0.011 mol) followed by crude amine obtained in Step-7 dissolved in dimethylformamide (10 mL). The reaction mixture was stirred at room temperature for 16 hours. Solvent was evaporated under reduced pressure, ethyl acetate (100 ml) was added to the residue and the mixture was then transferred to the separating funnel. The organic layer was washed with water (3×100 ml), dried over sodium sulfate, filtered and then solvent was evaporated under reduced pressure. The residue obtained was purified by column chromatography over a column of silica gel 60-120 mesh, using a gradient of 0:100-40:60 (Acetone: Hexane). The solvent from the combined fractions was evaporated under reduced pressure to obtain the 3.3 g of the titled compound as a white solid in 56% yield (over 2 steps).

Analysis:

Mass: 543(M+1); for Molecular weight: 542.6 and Molecular formula: $C_{25}H_{34}N_8O_6$ $^1$H NMR (CDCl$_3$, 400 MHz): δ 9.80 (bs, 1H), 8.60 (s, 1H), 7.43-7.35 (m, 5H), 5.42 -5.37 (m, 1H), 5.04(d, 1H, J=11.2 Hz), 4.89 (d, 1H, J=10.8 Hz), 4.40 -4.20 (m, 2H), 4.10 -3.88 (m, 4H), 3.30 (bs, 1H), 3.02 (d, 1H, J=11.2 Hz), 2.84-2.78 (m, 2H), 2.26 (dd, 1H, J=5.6, 13.2 Hz), 2.02 -1.93(m, 2H), 1.70 -1.60 (m, 1H), 1.47 (s, 9H).

Step 9: Synthesis of (2S,5R)-N-{[1-tert-butoxycarbonyl (2S,4S)-4-(2H-tetrazol-2-yl)pyrrolidin-2-yl]methyloxy}-6-hydroxy-7-oxo-1,6-diazabicyclo[3.2.1]octane-2-carboxamide: A solution of compound obtained in Step-8 (3.20 g, 5.90 mmol) in methanol (50 ml) containing 10% palladium over carbon (0.80 g, 50% wet) was hydrogenated at 50 psi for 1 hour under hydrogen atmosphere. The reaction mixture was then filtered, the filtrate was collected and solvent evaporated under reduced pressure to obtain the 2.54 g of the titled compound as white solid in 94% yield.

Analysis:

Mass: 453(M+1); for Molecular weight: 452.4and Molecular formula: $C_{18}H_{28}N_8O_6$ $^1$H NMR (CDCl$_3$, 400 MHz): δ 8.55 (s, 1H), 5.45 -5.35 (m, 1H), 4.40 -4.02 (m, 3H), 3.95-3.89 (m 3H), 3.73(bs, 1H), 3.18 (d, 1H, J=10.6 Hz), 2.97 (d, 1H, J=8.8 Hz), 2.90 -2.82 (m, 2H), 2.30 (dd, 1H, J=6.0, 14.4Hz), 2.20 -2.05 (m, 1H), 2.00 -1.90 (m, 1H), 1.81 -1.78 (m, 1H), 1.47 (s, 9H)

Step 10: Synthesis of (2S,5R)-N-{[1-tert-butoxycarbonyl (2S,4S)-4-(2H-tetrazol-2-yl)pyrrolidin-2-yl]methyloxy}-7-oxo-6-(sulfooxy)-1,6-diazabicyclo[3.2.1]octane-2-carboxamide: To a stirred solution of a compound obtained in Step-9 (2.5 g, 5.53 mmol) in pyridine (30 ml) was added sulfur trioxide pyridine complex (2.63 g, 16.5 mmol) and the reaction mixture stirred at room temperature for 16 hours. The solvent was evaporated under reduced pressure and the thick oil obtained was dissolved in 0.5 M potassium dihydrogen phosphate (150 ml) and stirred at room temperature for 30 minutes. The reaction mixture was then transferred to separating funnel, washed with ethyl acetate (3×100 ml). The aqueous layer was collected and transferred to round bottomed flask. To this tetrabutyl ammonium sulphate (1.877 g, 5.53 mmol) was added and the resulting mixture was stirred at room temperature for 1 hour. The reaction mixture was then extracted with dichloromethane (3×150 ml). The combined organic layer was dried over sodium sulfate, filtered and the solvent was evaporated under reduced pressure to obtain white foam. The white foam was purified by column chromatography over a column of silica-gel (60-120 mesh). The elution using a v/v gradient of 0:100-6:94(methanol: dichloromethane) was carried. The solvent of the combined fractions were evaporated to provide 2.7 g of the titled compound as white foam in 63% yield.

Analysis:

Mass: 531 (M-1); for Molecular weight: 532.5 and Molecular formula: $C_{18}H_{28}N_8O_9S$ $^1$H NMR (CDCl$_3$, 400 MHz): δ 9.80 (bs, 1H), 8.56 (s, 1H), 5.45 -5.36 (m, 1H), 4.40 -4.20 (m, 3H), 4.00 -3.88 (m, 2H), 3.41 -3.25 (m, 9H),2.87 -2.80 (m, 2H), 2.33-2.88 (m, 1H), 2.18 -2.14(m, 1H), 1.91 -1.85 (m, 1H), 1.75 -1.60 (m, 8H), 1.50 -1.40 (m, 17H), 1.35 -1.20 (m, 2H), 0.99 (t, 12H, J=6.8 Hz), 1.80 -1.60 (m, 2H);

Step 11: Synthesis of (2S,5R)-N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide: To a stirred solution of compound obtained in Step 10 (1.3 g, 1.67 mmol) in dichloromethane (5 ml) at −10° C. under argon atmosphere was slowly added trifluoroacetic acid (5 mL) and the reaction mixture was stirred at the same temperature for 2.5 hours. The reaction mixture was stirred with hexane (2×50 ml) and the hexane layer was decanted. Similarly, the reaction mixture was washed with diethyl ether (2×40 ml), dichloromethane (2×40 ml) and acetonitrile (2×40 ml). The obtained white solid was dried under reduced pressure (4 mm Hg) to obtain 0.6 g of (2S)-7-oxo-6-(sulfooxy)-N-{[(2S,4S)-4-(2H-tetrazol-2-yl)pyrrolidin-2-yllmethoxy}-1,6-diazabicyclo13.2.1]octane-2-carboxamide as a white solid in 84% yield.

Analysis:

Mass: 433 (M+1); for Molecular weight of 432.42 and Molecular Formula of $C_{13}H_{20}N_8O_7S$ $^1$H NMR (CDCl$_3$, 400 MHz): δ 9.05 (s, 1H), 5.80 -5.75 (m, 1H), 4.10 -4.00 (m, 3H), 3.92 -3.79 (m, 2H), 3.03(d, 1H, J=11.2 Hz), 2.92 (d, 1H, J=11.6 Hz), 2.91 -2.84(m, 1H), 2.38 -2.31 (m, 1H), 2.05 -1.95 (m, 1H), 1.90 -1.85 (m, 1H), 1.80 -1.60 (m, 2H).

Example 2

Trifluoro acetic acid salt of (2S,5R)-N-{[(2R,4S)-4-(morpholin-4-yl)pyrrolidin-2-yl]methoxy}-7-oxo-6-(sulfooxy)-1,6-diazabicyclo[3.2.1]octane-2-carboxamide

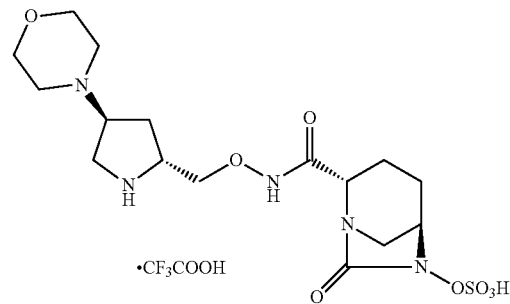

Step 1: Synthesis of 1-tert-butyl 2-methyl (2R,4R)-4-{[(4-nitrophenyl)sulfonyl]oxy}pyrrolidine-1,2-dicarboxylate : To a stirred solution of 1-tent-butyl 2-methyl (2R,4R)-4-hydroxypyrrolidine-1,2-dicarboxylate (prepared as per the procedure disclosed in International Patent Application No. 2011044057) (107 g, 0.437 mol) in dichloromethane (1100 ml) at 0° C. was added triethylamine (182.6 ml, 1.31 mol) over 10 minutes using addition funnel, followed by the lot wise addition of 4-nitrophenyl sulfonyl chloride (145 g, 0.655 mol) to the reaction mixture over 1.5 hr. Dimethylaminopyridine (3.04 g, 0.025 mol) was added to the resulted reaction mixture at 0° C. under continuous stirring. The reaction mixture was then allowed to attain 25° C. and stirred for 21 hours. The reaction mixture was then washed with 10% potassium hydrogen sulfate (500 ml), water (200 ml), saturated sodium hydrogen carbonate solution (500 ml), water (200 ml), and finally with brine (200 ml). The collected organic layer was dried over anhydrous sodium sulfate and solvent was evaporated under reduced pressure to obtain thick oil. Diethyl ether (100 ml) was added to the thick oil, stirred well and the solid separated was filtered and the residue was washed with hexane (200 ml). The obtained solid residue was dried under reduced pressure, yielded 1-tent-butyl 2-methyl (2R,4R)-4-[(4-nitrophenyl)sulfonyl] oxylpyrrolidine, as light brown powder, 150 g, 80% yield.

Analysis:

Mass: 431.2 (M+1); for Molecular weight: 430.4and Molecular formula: $C_{17}H_{22}N_2O_9$8;

$^1$H NMR (CDCl$_3$, 400 MHz): δ 8.42 (d, 1H, J=8.0 Hz), 8.11 (d, 1H, J=8.0 Hz), 5.21 (brs, 1H), 4.52-4.36 (m, 1H), 3.71 (s, 3H), 3.70-3.64(m, 2H), 2.56-2.42 (m, 2H), 1.43& 1.40 (s, 9H).

Step 2: Synthesis of 1-tert-butyl 2-methyl (2R,4S)-4-(morpholin-4-yl)pyrrolidine-1,2-dicarboxylate : To a stirred solution of compound 1-tent-butyl 2-methyl (2R,4R)-4-[(4-nitrophenyl)sulfonyl]oxy]pyrrolidine (15.0 g, 0.035 mol) in acetonitrile (60 ml) was added morpholine (6.10 ml, 0.070 mol). The reaction mixture was heated at 80° C. for 16 hours. Reaction mixture was cooled to 25° C. and filtered the reaction mixture. Filtrate was concentrated and the residue was taken in ethyl acetate (300 ml) and the solution was washed with water (2×100 ml). The organic layer was then collected, dried over anhydrous sodium sulfate, filtered and the solvent was evaporated under reduced pressure. The residue obtained was then purified by silica gel (60-120 mesh size) column chromatography using 60% Ethyl acetate: Hexane mixture as an eluant to get required compound. The combined fractions were evaporated to obtain 1-tent-butyl 2-methyl (2R,4S)-4-(morpholin-4-yl)pyrrolidine-1,2-dicarboxylate as light yellow oil (6 g, 55%).

Analysis

Mass: 315.0 (M+1); for molecular weight: 314.38 and Molecular formula: $C_{15}H_{26}N_2O_5$;

$^1$H NMR (CDCl$_3$, 400 MHz): δ 4.48-4.32 (m, 1H), 3.88-3.80 (m, 1H), 3.78-3.68 (m, 4H), 3.74(s, 3H), 3.26-3.16 (m, 1H), 3.04×2.92 (m, 1H), 2.54×2.38 (m, 4H), 2.20-2.10 (m, 2H), 1.46 & 1.41 (s, 9H).

Step 3: Synthesis of tert-butyl (2R,4S)-2-(hydroxymethyl)-4-(morpholin-4-yl)pyrrolidine-1-carboxylate : To a stirred solution of lithium aluminium hydride (1.45 g, 0.038 mol) in tetrahydrofuran (60 ml) at 0° C. was added dropwise a solution of compound 1-tent-butyl 2-methyl (2R,4S)-4-(morpholin-4-yl)pyrrolidine-1,2-dicarboxylate (6.0 g, 0.019 mol) in tetrahydrofuran (60 ml). The resulting mixture was stirred for 15 minutes at the same temperature. Saturated aqueous solution of sodium sulfate was then slowly added to the reaction mixture and stirred until the entire grey solid was turned in to white solid. The reaction mixture was then filtered through celite, the filtrate was collected and solvent was evaporated under reduced pressure to obtain the titled compound as colorless oil, 5.0 g, 91% yield.

Analysis:

Mass: 287.1 (M+1); for Molecular weight: 286.3and Molecular formula: $C_{14}H_{26}N_2O_4$.

Step 4: Synthesis of tert-butyl (2R,4S)-4-(morpholin-4-y0-2-{[(1,3-dioxo-1,3-dihydro-2H-isoindol-2-y0oxy]methyl}pyrrolidine-1-carboxylate : To a stirred solution of tert-butyl (2R,4S)-2-(hydroxymethyl)-4-(morpholin-4-yl)pyrrolidine-1-carboxylate (5.0 g, 0.017 mol) in tetrahydrofuran (50 ml) was added triphenyl phosphine (8.20 g, 0.031 mol), N-hydroxyphthalimide (4.27 g, 0.026 mol) and diisopropyl azodicarboxylate (6.10 ml, 0.031 mol). The resulting mixture was stirred at 25° C. for 16 hours. Solvent was evaporated and the residue obtained was purified by silica gel(60-120 mesh size) using 60% Ethyl acetate: Hexane mixture as an eluant, the pure fractions upond concentration yielded the required compound, 7 g as colorless oil, 93% yield.

Analysis:

Mass: 432.3(M+1); for Molecular weight: 431.49 and Molecular formula: $C_{22}H_{29}N_3O_6$.

Step 5: Synthesis of tert-butyl (2R,4S)-2-[(aminooxy)methyl]-4-(morpholin-4-yl)pyrrolidine-1-carboxylate : To a stirred solution of tert-butyl (2R,4S)-4-(morpholin-4-yl)-2-{[(1,3-dioxo-1,3-dihydro-2H-isoindol2-yl)oxy]methyl}pyrrolidine-1-carboxylate (7.0 g, 0.016 mol) in dichloromethane (140 ml) was added hydrazine hydrate (1.58 ml, 0.032 mol) and the reaction mixture was stirred at room temperature for 2 hours. The white solid precipitated out in the reaction mixture was filtered off and the filtrate was diluted with dichloromethane (50 ml) and washed with water (20 ml). The organic layer was then collected, dried over anhydrous sodium sulfate, filtered and the solvent was evaporated under reduced pressure to give the titled compound, which was used in next reaction without further purification.

Analysis:

Mass: 302.2 (M+1); for Molecular weight: 301.39 and Molecular formula: $C_{14}H_{27}N_3O_4$. -Step 6: Synthesis of (2S,5R)-N-{[1-tert-butoxycarbonyl (2R,4S)-4-(morpholin-4-yl)pyrrolidin-2-yl]methoxy}-6-benzyloxy-7-oxo-1,6-diazabicyclo[3.2.1]octane-2-carboxamide : To a stirred solution of sodium salt of (2S,5R)-6-benzyloxy-7-oxo-1,6-diaza-bicyclo[3.2.1] octane-2-carboxylic acid, (prepared as per the procedure disclosed in International Patent Application No. PCT/IB2013/059264) (2.97 g, 0.010 mol) in dimethylformamide (20 ml) were successively added N-methyl morpholine (2.22 ml, 0.020 mol), EDC. HCl (2.87 g, 0.015 mol), HOBt (1.34 g, 0.010 mol) followed by addition of a solution of tert-butyl (2R,4S)-2-[(aminooxy)methyl]-4-(morpholin-4-yl)pyrrolidine-1-carboxylate (3.0 g, 0.010 mol) in dimethylformamide (10 ml). The reaction mixture was stirred at 25° C. for 19 hours. Solvent was evaporated under reduced pressure, and the residue was taken in dichloromethane (200 ml) and the solution was washed with water (30 ml). The organic layer was then collected, dried over anhydrous sodium sulfate, filtered and the solvent was evaporated under reduced pressure. The residue obtained was then purified by silica gel (60-120 mesh size) column chromatography using 50% Ethyl acetate: Dichloromethane mixture as an eluant to get required compound. The solvent from the combined fractions were evaporated under reduced pressure yielded the titled compound, 2.0 g as a white solid, 36% yield.

Analysis:

Mass: 560.4(M+1); for Molecular weight: 559 and Molecular formula: $C_{28}H_{41}N_5O_7$ $^1$H NMR (CDCl$_3$, 400 MHz): δ 10.35 (brS,1H), 7.45-7.30 (m, 5H), 5.06 (d, 1H, J=11.6 Hz), 4.91 (d, 1H, J=11.6 Hz), 4.34-4.24(m, 1H), 4.10-3.78 (m, 3H), 3.78-3.64(m, 4H), 3.62-3.52 (m, 1H), 3.36-3.24(m, 2H), 3.06-2.76 (m, 3H), 2.56-2.40 (m, 4H), 2.38-2.24(m, 1H), 2.06-1.88 (m, 4H), 1.70-1.60 (m, 1H), 1.45(s, 9H).

Step 7: Synthesis of (2S,5R)-N-{[1-tert-butoxycarbonyl (2R,4S)-4-(morpholin-4-yl)pyrrolidin-2-yl]methoxy}-6-hydroxy-7-oxo-1,6-diazabicyclo[3.2.1]octane-2-carboxamide: A solution of (2S,5R)-N-{[1-tert-butoxycarbonyl (2R, 4S)-4-(morpholin-4-yl)pyrrolidin-2-yl]methoxy}-6-benzyloxy-7-oxo-1,6-diazabicyclo[3.2.1]octane-2-carboxamide (2.0 g, 0.0036 mol) in methanol (20 ml) containing 10% palladium over carbon (0.40 g, 50% wet) was hydrogenated at 50 psi for 1 hour under hydrogen atmosphere. The reaction mixture was then filtered through celite bed, the collected filtrate was evaporated under reduced pressure, yielded 1.5 g of the titled compound as white solid, 90% yield.

Analysis:

Mass: 470.4(M+1); for Molecular weight: 469 and Molecular formula: $C_{21}H_{35}N_5O_7$ Step 8: Synthesis of tetrabutylammonium salt of (2S,5R)-N-{[1-tert-butoxycarbonyl (2R,4S)-4-(morpholin-4-yl)pyrrolidin-2-yl]methoxy}-7-oxo-6-(sulfooxy)-1,6-diazabicyclo[3.2.1]octane-2-carboxamide: To a stirred solution of (2S, 5R)-N-{[1-tert-butoxycarbonyl (2R,4S)-4-(morpholin-4-yl) pyrrolidin-2-yl]methoxy}-6-hydroxy-7-oxo-1,6-diazabicyclo[3.2.1]octane-2-carboxamide (1.5 g, 0.0032 mol) in dimethylformamide (15 ml) was added sulfur trioxide: dimethylformamide complex (1.0 g, 0.0064 mol) under stirring at temperature of about 0 °C. The reaction mixture was stirred at 0° C. for 10 minutes and then allowed to warm to 25° C. After 1 hr of stirring a solution of tetra butyl ammonium acetate (2.89 g, 0.0096 mol) in water (8 ml) was added to the reaction mixture under continuous stirring. After completion of 1 hr stirring the solvent from the reaction mixture was evaporated under reduced pressure to obtain an oily residue. The residue obtained was then purified by silica gel(60-120 mesh size) column chromatography using 6% Methanol: DCM mixture as an eluant to get required compound. The solvent of the combined fractions were evaporated to provide 1.2 g of the titled compound as white solid, 47% yield.

Analysis:
Mass: 548.4(M-1) as free acid; for Molecular weight: 791.07 and Molecular formula: $C_{37}H_{70}N_6O_{10}S$
$^1$H NMR (CDCl$_3$, 400 MHz): δ 10.42 (brS,1H), 4.38-4.28 (m, 1H), 3.98-3.92 (m, 1H), 3.86-3.68 (m, 5H), 3.62-3.52 (m, 1H), 3.42-3.20 (m, 10H), 2.98-2.84(m, 2H), 2.58-2.32 (m, 5H), 2.24-2.14(m, 1H), 1.96-1.84(m, 2H), 1.84-1.62 (m, 12H), 1.56-1.42 (m, 17H), 1.06-0.97 (m, 12H).

Step 9: Synthesis of Trifluoro acetic acid salt of (2S,5R)-N-{[(2R,4S)-4-(morpholin-4-yl)pyrrolidin-2-yl]methoxy}-7-oxo-6-(sulfooxy)-1,6-diazabicyclo[3.2.1]octane-2-carboxamide: To a stirred solution of compound obtained in step 8 (1.2 g, 1.67 mmol) in dichloromethane (9 ml) at -10° C. under argon atmosphere was slowly added trifluoroacetic acid (9 mL) and the reaction mixture was stirred at −10° C. for 30 minutes. The reaction mixture was stirred with hexane (3×5 ml) and the hexane layer was decanted. Similarly, the reaction mixture was washed with diethyl ether (3×5 ml), dichloromethane (2×5 ml). The obtained white solid was dried under reduced pressure (4 mm Hg) to obtain Trifluoro acetic acid salt of (2S,5R)-N-{[(2R,4S)-4-(morpholin-4-yl) pyrrolidin-2-yl]methoxy}-7-oxo-6-(sulfooxy)-1,6-diazabicyclo[3.2.1]octane-2-carboxamide as a white solid, 0.455 g, 53% yield.

Analysis:
Mass: 448.3(M-H); for Molecular weight of 563.50 and Molecular Formula of $C_{16}H_{27}N_5O_8S.C_2HO_2F_3$
$^1$H NMR (DMSO-d$_6$, 400 MHz): δ 11.82 (s, 1H), 9.48 (br S,1H), 9.08 (br S,2H), 4.08-3.94 (m, 5H), 3.86-3.62 (m, 6H), 3.44-3.36 (m, 2H), 3.20-2.96 (m, 5H), 2.36-2.26 (m, 2H), 2.12-1.64(m, 4H).
Purity as determined by HPLC: 95.76%

Example 3

(2S,5R)-N-{[(2S,4R)-4-(1H-pyrazol-1-yl)pyrrolidin-2-yl]carbonyl}-7-oxo-6-(sulfooxy)-1,6-diazabicyclo [3.2.1]octane-2-carbohydrazide

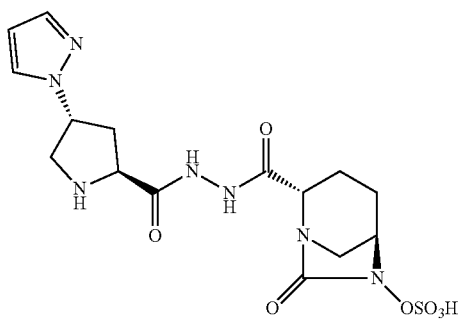

Step-1: Synthesis of tert-butyl (2S,4R)-2-(hydrazinylcarbonyl)-4-(1H-pyrazol-1-yl)pyrrolidine-1-carboxylate: To a clean dry flask was charged a solution of 1-tent-butyl 2-methyl (2S,4R)-4-(1H-pyrazol-1-yl)pyrrolidine-1,2-dicarboxylate (3.0 g, 10.20 mmol) in 30 mL ethanol. Hydrazine hydrate (2.6 mL, 51.02 mmol) was added to the solution and the solution was heated under reflux. The reaction was monitored by thin layer chromatography using mixture of ethyl acetate and hexane (1:1). After complete consumption of starting material the volatiles were removed under reduced pressure to obtain yellow oil. The compound was dried under reduced pressure to obtain 2.7 g of the titled in 77% yield; and was used as such in the next reaction without further purification.

Analysis:
Mass: 296.4(M+1); for Molecular weight: 295.34and Molecular formula: $C_{13}H_{21}N_5O_3$.

Step-2: Synthesis of (2S,5R)-6-(benzyloxy)-N'-{[(2S,4R)-1-(tert-butoxycarbonyl)-4-(1H-pyrazol-1-yl)pyrrolidin-2-yl]carbonyl}-7-oxo-1,6-diazabicyclo[3.2.1]octane-2-carbohydrazide: To a solution of sodium salt of (2S,5R)-6-benzyloxy-7-oxo-1,6-diaza-bicyclo [3.2.1] octane-2-carboxylic acid (2.73 g, 9.15 mmol) in dimethylformamide (30 mL) were added successively EDC.HCl (2.62 g, 13.73 mmol), N-methylmorpholine (1.25 mL, 9.15 mmol) and HOBT (1.24 g, 9.15 mmol) at 0° C. The solution was stirred for 15 minute and compound of step-1 (2.7 g, 9.15 mmol) was added to the solution at 0° C. The reaction was allowed to warm to room temperature and it was further stirred overnight (18 hours) at room temperature. The resulting mixture was poured into cold water (340 mL), stirred well and the separated product was filtered. The solid was further purified by column chromatography using 60-120 mesh silica gel (Ethyl acetate: Hexane 1:1). The solvent from the combined fractions was evaporated under reduced pressure to obtain 2.22 g of the titled compound in 45% yield.

Analysis:
Mass: 552.3(M-1); for Molecular weight: 553.62 and Molecular formula: $C_{27}H_{35}N_7O_6$
$^1$H-NMR (400 MHz, CDCl$_3$): δ=9.20 (s, 1H), 8.35 (s, 1H), 8.27 (s, 1H), 7.54(s, 1H), 7.43-7.36 (m, 5H), 6.24(s, 1H), 5.06 (d, J=10.8 Hz, 1H), 5.01 (d, J=7.6 Hz, 1H), 4.92 (d, J=10.8 Hz, 1H), 4.64(d, J=7.6 Hz, 1H), 4.02 (d, J=7.2 Hz, 1H), 3.84(d, J=7.6 Hz, 1H), 3.29 (s, 1H), 3.25 (d, J=12.0 Hz, 1H), 3.21 -3.07 (m, 2H), 2.89 -2.72 (m, 1H), 2.35 -2.27 (m, 1H), 2.04-1.94(m, 2H), 1.65 -1.58 (m, 2H), 1.47 (s, 9H).

Step-3: Synthesis of (2S,5R)-6-hydroxy-N'-{[(2S,4R)-1-(tert-butoxycarbonyl)-4-(1H-pyrazol-1-yl)pyrrolidin-2-yl]carbonyl}-7-oxo-1,6-diazabicyclo[3.2.1]octane-2-carbohydrazide: A solution of product obtained in step-2 (2.22 g, 4.01 mmoles) in methanol (20 mL) containing 10% Pd/C (0.6 g) was hydrogenated in 50 psi at 25-30° C. The progress of reaction was monitored by thin layer chromatography using mixture of ethyl acetate and hexane (1:1). After complete consumption of starting material the reaction mixture was filtered through celite bed and washed with methanol (2×10 mL). The combined filtrate was concentrated under reduced pressure to obtain the titled compound (1.3 g, 70%). This was used as such for the next reaction.

Analysis:
Mass: 462.3(M-1); for Molecular weight: 463.5 and Molecular formula: $C_{20}H_{29}N_7O_6$.

Step-4: Synthesis of tetrabutylammonium salt of (2S,5R)-6-(sulfooxy)-N'-{[(2S,4R)-1-(tert-butoxycarbonyl)-4-(1H-pyrazol-1-yl)pyrrolidin-2-yl]carbonyl}-7-oxo-1,6-diazabicyclo[3.2.1] octane-2-carbohydrazide: To a stirred solution of compound obtained in Step-3(1.3 g, 2.81 mmoles) in pyridine (13 mL) was added sulfur trioxide pyridine complex (2.23 g, 14.04 mmol) and strring continued further at 30-35° C. The progress of reaction was monitored by Mass. The insoluble reagent was removed by filtration on celite bed, the residue was washed with fresh pyridine (2×8 mL). The combined filtrate was concentrated under reduced pressure and dried at 4 mmHg The residue obtained was diluted with 5% $KH_2PO_4$ solution (100 mL) and stirred for 0.5 hour. The solution was washed with ethyl acetate (2×50 mL). The aqueous reaction mixture was taken in flask and tetrabutyl ammonium hydrogen sulfate (1.14 g, 3.37 mmoles) was added to it under stirring. The reaction mixture was stirred for 1 hour and extracted with dichloromethane (2×100 mL). The dichloromethane extract was dried on anhydrous sodium sulfate and volatiles were removed under reduced pressure to obtain crude product. This was purified by column chromatography using 60-120 mesh silica gel using a mixture of dichloromethane and methanol (10:1) as solvent. The solvent from combined fractions was evaporated under reduced pressure to obtain the titled compound as semisolid (1.2 g, 55%).

Analysis:

Mass: 542.23(M-1); for Molecular weight: 785.02 and Molecular formula: $C_{36}H_{64}N_8O_9S$;

Purity as determined by HPLC: 94.33%;

$^1$H-NMR (400MHz, $CDCl_3$): δ 9.22 (s, 1H), 8.42 (s, 1H), 7.54(s, 1H), 7.44(d, J=2.0 Hz, 1H), 6.25 (t, J=2.0 Hz, 1H), 5.04(t, J=7.4Hz, 1H), 4.65 (d, J=8.0 Hz, 1H), 4.36 (s, 1H), 3.99 (d, J=7.6 Hz, 1H), 3.85 (d, J=7.2 Hz, 1H), 3.40 (d, J=10.8 Hz, 1H), 3.32 -3.28 (m, 8H), 3.18 (d, J=11.6 Hz, 1H), 2.88 -2.78 (m, 1H), 2.64-2.58 (m, 1H), 2.37 (dd, J=14.8 Hz, 8.0 Hz, 1H), 2.32 -2.28 (m, 1H), 1.94-1.88 (m, 1H), 1.72 -1.63(m, 9H), 1.49 -1.41 (m, 12 H), 1.28 -1.24 (m, 3H), 1.03-0.99 (m, 8H).

Step-5: Synthesis of (2S,5R)-N-{[(2S,4R)-4-(1H-pyrazol-1-yl)pyrrolidin-2-yl]carbonyl}-7-oxo-6-(sulfooxy)-1,6-diazabicyclo[3.2.1]octane-2-carbohydrazide: The above obtained tetrabutylammonium acetate compound (1.2 g, 1.52 mmol) was dissolved in dichloromethane (7.5 mL) and the solution was cooled to −10° C. and trifluoroacetic acid (5 mL) was added drop wise to the solution. The reaction was monitored by ES-MS analysis. The temperature of the solution maintain at −10 to −5 ° C. After completion of the reaction, excess hexane (40 mL) was added to the reaction mixture. The hexane layer was decanted and the oily residue was washed thoroughly by hexane (20 mL), and di-ethyl ether (20 mL). The solid residue formed was further washed with ether, acetonitrile and lastly dichloromethane (10 ml each solvent). The residue was dried under reduced pressure to obtain the titled compound as a white solid (0.465 g, 75%). The compound was characterised by ES-MS, H-NMR and HPLC purity analysis.

Analysis:

Mass: 444.2 (M-1); for Molecular weight: 443.44and Molecular formula: $C_{15}H_{21}N_7O_7S$;

$^1$H-NMR (400 MHz, DMSO-$d_6$): δ10.49 (s, 1H), 10.20 (br S,1H), 9.92 (br S,1H), 9.18 (s, 1H), 7.89 (s, 1H), 7.59 (s, 1H), 6.34(s, 1H), 5.29(s, 1H), 4.62-4.59 (m, 1H), 4.04(s, 1H), 3.89-3.79 (m, 2H), 3.62-3.52 (m, 1H), 3.06-3.03(m, 1H), 2.63×2.58 (m, 1H), 2.45-2.41 (m, 1 H), 2.05-1.82 (m, 2H), 1.75-1.54(m, 2H);

Purity as determined by HPLC: 96.61%

The compounds of Examples 4to 16 (Table 1) were prepared using the procedure described in Example 1 and using appropriate compound of Formula (VII) in place of tetrazole in Step 4(As outlined in Scheme 1). Similarly, the compounds of Examples 17 to 22 (Table 1) were prepared using the procedure described in Example 2 and using appropriate compound of Formula (VII) in place of morpholine in Step 2 (As outlined in Scheme 1) and the compounds of Examples 23to 34 (Table 1) were prepared using the procedure described in Example 3.

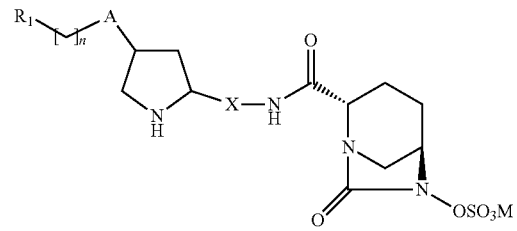

Formula (I)

TABLE 1

| Example No. | Compound of Formula (I) | Compound of Formula (IX) | $^1$H NMR (DMSO-$d_6$) | Mass (as free acid) Molecular Formula |
|---|---|---|---|---|
| 4. | | | δ 11.79 (bs, 1H), 9.53 (s, 1H), 9.35 (bs, 2H), 5.60-5.54 (m, 1H), 4.20-4.00 (m, 4H), 3.90-3.80 (m, 2H), 3.73 (dd, 1H, J = 5.6, 12.4 Hz), 3.05 (d, 1H, J = 12.0 Hz), 2.97 (d, 1H, J = 12.0 Hz), 2.88-2.81 (m, 1H), 2.29-2.21 (m, 1H), 2.12 = 2.00 (m, 1H), 1.96-1.81 (m, 1H), 1.80-1.60 (m, 2H). | 433 (M + 1) $C_{13}H_{20}N_8O_7S$ |

TABLE 1-continued

| Example No. | Compound of Formula (I) | Compound of Formula (IX) | ¹H NMR (DMSO-d₆) | Mass (as free acid) Molecular Formula |
|---|---|---|---|---|
| 5. | | | δ 11.7 (s, 1H), 9.31 (bs, 2H), 7.91 (s, 2H), 5.51-5.46 (m, 1H), 4.11-4.03 (m, 4H), 3.83-3.73 (m, 3H), 3.05 (d, 1H, J = 12.0 Hz), 2.95 (d, 1H, J = 12.0 Hz), 2.80-2.73 (m, 1H), 2.29-2.21 (m, 1H), 2.07-2.03 (m, 1H), 1.95-1.89 (m, 1H), 1.75-1.67 (m, 2H). | 432 (M + 1) $C_{14}H_{21}N_7O_7S$ |
| 6. | | | δ 11.80 (bs, 1H), 9.15 (bs, 2H), 8.29 (s, 1H), 7.82 (s, 1H), 5.50-5.40 (m, 1H), 4.20-4.00 (m, 4H), 3.90-3.79 (m, 2H), 3.70 (dd, 1H, J = 6.0, 12.4 Hz), 3.04 (d, 1H, J = 11.6 Hz), 2.97 (d, 1H, J = 11.6 Hz), 2.82-2.75 (m, 1H), 2.22-2.15 (m, 1H), 2.08-2.00 (m, 1H), 1.95-1.84 (m, 1H), 1.80-1.60 (m, 2H). | 432 (M + 1) $C_{14}H_{21}N_7O_7S$ |
| 7. | | | δ 11.79 (bs, 1H), 9.40 (bs, 2H), 9.01 (bs, 1H), 7.81 (s, 1H), 7.65 (s, 1H), 5.22 (bs, 1H), 4.20-4.00 (m, 4H), 3.95-3.78 (m, 2H), 3.60 (dd, 1H, J = 4.4, 12.4 Hz), 3.04 (d, 1H, J = 12.0 Hz), 3.98 (d, 1H, J = 12.0 Hz), 2.50-2.35 (m, 2H), 2.05-2.00 (m, 1H), 1.97-1.84 (m, 1H), 1.80-1.60 (m, 2H). | 431 (M + 1) $C_{17}H_{23}F_3N_6O_9S$ |
| 8. | | | δ 11.74 (bs, 1H), 9.19 (bs, 2H), 7.84 (s, 1H), 7.74 (d, 1H, J = 6.0 Hz), 6.28 (s, 1H), 5.23-5.15 (m, 1H), 4.30-3.90 (m, 4H), 3.80-3.50 (m, 3H), 3.03 (d, 1H, J = 12.0 Hz), 2.95 (d, 1H, J = 12.0 Hz), 2.65-2.58 (m, 1H), 2.31-2.19 (m, 1H), 2.08-2.01 (m, 1H), 1.94-1.80 (m, 1H), 1.80-1.60 (m, 2H). | 431 (M + 1) $C_{15}H_{22}N_6O_7S$ |
| 9. | | | δ 11.76 (s, 1H), 9.26 (bs, 2H), 8.63 (s, 1H), 8.07 (s, 1H), 5.35-5.20 (m, 1H), 4.10-3.98 (m, 4H), 3.85-3.70 (m, 2H), 3.60-3.50 (m, 1H), 3.03 (d, 1H, J = 12.0 Hz), 2.96 (d, 1H, J = 12.0 Hz), 2.70-2.65 (m, 1H), 2.10-2.01 (m, 2H), 1.96-1.82 (m, 1H), 1.80-1.60 (m, 2H). | 432 (M + 1) $C_{14}H_{21}N_7O_7S$ |
| 10. | | | δ 11.82 (s, 1H), 9.90 (bs, 2H), 8.99 (s, 1H), 7.84 (s, 1H), 7.63 (s, 1H), 5.25-5.18 (m, 1H), 4.14-3.97 (m, 4H), 3.83-3.78 (m, 2H), 3.60-3.55 (m, 1H), 3.05 (d, 1H, J = 11.6 Hz), 2.99 (d, 1H, J = 11.6 Hz), 2.80-2.75 (m, 1H), 2.15-2.00 (m, 2H), 1.96-1.82 (m, 1H), 1.80-1.60 (m, 2H). | 431 (M + 1) $C_{17}H_{23}F_3N_6O_9S$ |

TABLE 1-continued

| Example No. | Compound of Formula (I) | Compound of Formula (IX) | $^1$H NMR (DMSO-$d_6$) | Mass (as free acid) Molecular Formula |
|---|---|---|---|---|
| 11. | | | δ 11.77 (s, 1H), 9.48 (brs, 1H), 9.32 (brs, 1H), 9.13 (s, 1H), 5.86 (brs, 1H), 4.24-4.02 (m, 4H), 4.00-3.80 (m, 3H), 3.08-2.96 (m, 2H), 2.70-2.62 (m, 1H), 2.48-2.38 (m, 1H), 2.08-1.88 (m, 2H), 1.80-1.64 (m, 2H). | 431.30 (M − 1) $C_{13}H_{20}N_8O_7S$ |
| 12. | | | δ 11.77 (s, 1H), 9.34 (brs, 1H), 9.12 (s, 1H), 7.10 (brs, 1H), 5.86 (brs, 1H), 4.20-4.04 (m, 4H), 3.98-3.72 (m, 3H), 3.10-2.96 (m, 2H), 2.68-2.60 (m, 1H), 2.50-2.32 (m, 1H), 2.10-1.52 (m, 4H). | 431.30 (M − 1) $C_{13}H_{20}N_8O_7S$ |
| 13. | | | δ 11.78 (s, 1H), 9.38 (brs, 1H), 9.28 (brs, 1H), 7.93 (s, 2H), 5.54 (s, 1H), 4.20-4.02 (m, 4H), 3.90-3.74 (m, 3H), 3.08-2.94 (m, 2H), 2.62-2.24 (m, 2H), 2.10-1.88 (m, 2H), 1.80-1.64 (m, 2H). | 430.30 (M − 1) $C_{14}H_{21}N_7O_7S$ |
| 14. | | | δ 11.76 (s, 1H), 9.42 (brs, 1H), 9.23 (brs, 1H), 8.28 (s, 1H), 7.83 (s, 1H), 5.50 (s, 1H), 4.24-4.02 (m, 4H), 3.94-3.72 (m, 3H), 3.08-2.96 (m, 2H), 2.62-2.30 (m, 2H), 2.10-1.64 (m, 4H). | 430.30 (M − 1) $C_{14}H_{21}N_7O_7S$ |
| 15. | | | δ 11.77 (s, 1H), 9.36 (brs, 1H), 9.16 (brs, 1H), 8.66 (s, 1H), 8.12 (s, 1H), 5.40 (s, 1H), 4.28-4.18 (m, 1H), 4.16-3.98 (m, 5H), 3.62-3.54 (m, 1H), 3.08-2.96 (m, 2H), 2.44-2.22 (m, 2H), 2.10-1.64 (m, 4H). | 430.30 (M − 1) $C_{14}H_{21}N_7O_7S$ |
| 16. | | | δ 11.82 (bs, 1H), 8.46 (s, 1H), 6.79 (s, 1H), 8.07, 5.06-5.02 (m, 1H), 4.20-4.00 (m, 3H), 3.95-3.86 (m, 1H), 3.83 (d, 1H, J = 6.4 Hz), 3.76-3.70 (m, 1H), 3.52-3.48 (m, 1H), 3.40-3.35 (m, 1H), 3.06 (d, 1H, J = 10.4 Hz), 2.97 (d, 1H, J = 11.6 Hz), 2.73 2.64 (m, 1H), 2.08-1.68 (m, 4H). | 446 (M + 1) $C_{17}H_{24}F_3N_7O_9S$ |

TABLE 1-continued

| Example No. | Compound of Formula (I) | Compound of Formula (IX) | $^1$H NMR (DMSO-$d_6$) | Mass (as free acid) Molecular Formula |
|---|---|---|---|---|
| 17. | 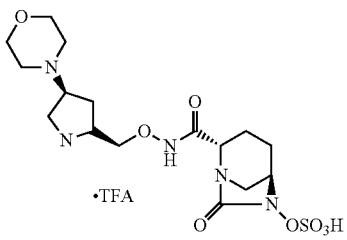 ·TFA | 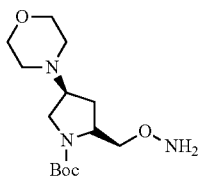 | δ 11.85 (s, 1H), 9.22 (brs, 2H), 7.35 (brs, 2H), 4.42-4.00 (m, 7H), 3.98-3.46 (m, 6H), 3.28-2.96 (m, 5H), 2.24-1.62 (m, 6H). | 448.30 (M − 1) $C_{18}H_{27}F_3N_5O_{10}S$ |
| 18. | 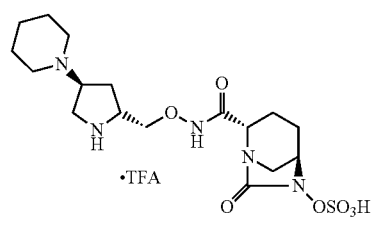 ·TFA | 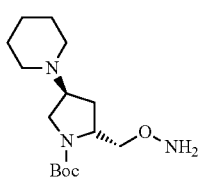 | δ 11.81 (s, 1H), 9.98 (brs, 1H), 9.78 (brs, 1H), 9.23 (brs, 1H), 4.12-3.94 (m, 4H), 3.82-3.38 (m, 6H), 3.10-2.92 (m, 4H), 2.48-2.38 (m, 1H), 2.26-2.14 (m, 1H), 2.10-2.00 (m, 2H), 1.98-1.57 (m, 8H). | 446.40 (M − 1) $C_{19}H_{28}F_3N_5O_9S$ |
| 19. | 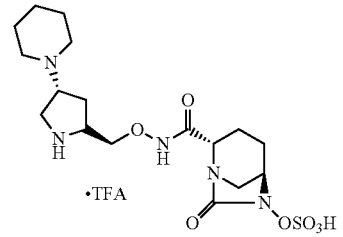 ·TFA | 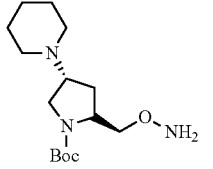 | δ 11.81 (s, 1H), 9.79 (brs, 1H), 9.59 (brs, 1H), 9.15 (brs, 1H), 4.12-3.94 (m, 4H), 3.86-3.70 (m, 2H), 3.52-3.32 (m, 4H), 3.18-2.88 (m, 4H), 2.44-2.30 (m, 1H), 2.26-2.14 (m, 1H), 2.24-2.12 (m, 1H), 2.06-1.98 (m, 1H), 1.98-1.52 (m, 8H). | 446.40 (M − 1) $C_{19}H_{28}F_3N_5O_9S$ |
| 20. | 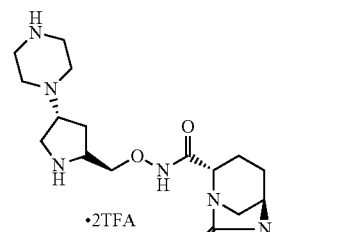 ·2TFA | 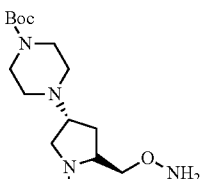 | δ 11.76 (s, 1H), 9.16 (brs, 1H), 8.86 (brs, 2H), 8.53 (brs, 2H), 4.30-3.52 (m, 10H), 3.52-3.38 (m, 2H), 3.24-2.98 (m, 6H), 2.72-2.44 (m, 2H), 2.12-1.54 (m, 4H). | 447.40 (M − 1) $C_{20}H_{30}F_6N_6O_{11}S$ |
| 21. | 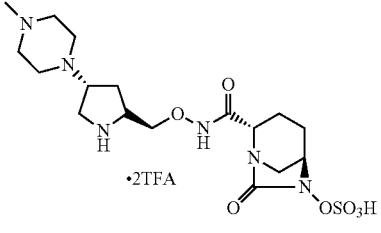 ·2TFA | 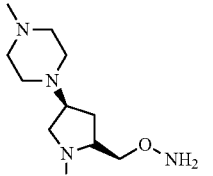 | δ 11.74 (s, 1H), 9.88 (brs, 2H), 9.36 (brs, 1H), 8.96 (brs, 1H), 4.08-3.79 (m, 5H), 3.50-3.38 (m, 4H), 3.22-2.92 (m, 9H), 2.79 (s, 3H), 2.40-2.26 (m, 2H), 2.10-1.52 (m, 4H). | 461.3 (M − 1) $C_{21}H_{31}F_6N_6O_{11}S$ |
| 22. | 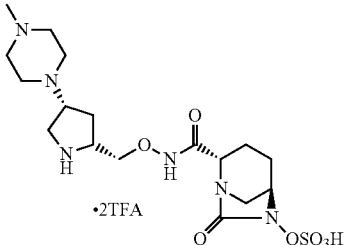 ·2TFA | 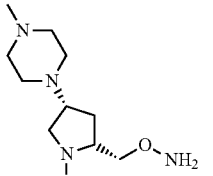 | δ 11.74 (s, 1H), 9.63 (brs, 2H), 9.26 (brs, 1H), 8.89 (brs, 1H), 4.06-3.78 (m, 5H), 3.50-3.36 (m, 4H), 3.22-2.90 (m, 9H), 2.79 (s, 3H), 2.38-2.26 (m, 2H), 2.08-1.52 (m, 4H). | 461.3 (M − 1) $C_{21}H_{31}F_6N_6O_{11}S$ |

TABLE 1-continued

| Example No. | Compound of Formula (I) | Compound of Formula (IX) | $^1$H NMR (DMSO-$d_6$) | Mass (as free acid) Molecular Formula |
|---|---|---|---|---|
| 23. | | | δ 10.54 (s, 1H), 10.23 (s, 1H), 9.78-9.32 (s, 1H), 9.08 (s, 1H), 5.84-5.79 (m, 1H), 4.53-4.48 (t, 1H, J = 9.2 Hz), 4.03 (s, 1H), 3.95-3.79 (m, 3H), 3.23-3.15 (m, 2H), 3.05-3.02 (m, 1H), 2.71-2.63 (m, 1H), 2.07-2.00 (m, 1H), 1.90-1.60 (m, 4H). | 444.2 (M − 1) $C_{13}H_{19}N_9O_7S$ |
| 24. | | | δ 10.56 (s, 1H), 10.25 (s, 1H), 9.4 (s, 2H), 5.57-5.52 (m, 1H), 4.50-4.45 (t, 1H, J = 9.2 Hz), 4.02 (s, 1H), 3.89-3.82 (m, 2H), 3.74-3.68 (m, 1H), 3.19-3.01 (m, 4H), 2.06-1.99 (m, 1H), 1.71-1.55 (m, 4H). | 444.2 (M − 1) $C_{13}H_{19}N_9O_7S$ |
| 25. | | | δ 7.89 (s, 2H), 5.56-5.52 (m, 1H), 4.52-4.472 (m, 1H), 4.04 (bs, 1H), 4.00 (bs, 1H), 3.91-3.73 (m, 3H), 3.19-3.05 (m, 3H), 2.07-1.57 (m, 5H). | 443.2 (M − 1) $C_{14}H_{20}N_8O_7S$ |
| 26. | | | δ 10.53 (s, 1H), 10.25 (s, 1H), 9.51 (bs, 2H), 8.28 (s, 1H), 7.82 (s, 1H), 5.54-5.51 (m, 1H), 4.55-4.45 (m, 1H), 4.04 (bs, 1H), 3.91-3.62 (m, 3H), 3.22-3.03 (m, 3H), 2.45-2.40 (m, 1H), 2.05-1.57 (m, 4H). | 443.1 (M − 1) $C_{14}H_{20}N_8O_7S$ |
| 27. | | | δ 10.48-10.44 (m, 1H), 10.24-10.22 (m, 1H), 9.60-9.30 (s, 2H), 7.89-7.86 (m, 1H), 7.60-7.55 (m, 1H), 6.33-6.30 (m, 1H), 5.26-5.23 (m, 1H), 4.44-4.40 (t, 1H, J = 8 Hz), 4.05 (s, 1H), 3.90-3.71 (m, 2H), 3.62-3.52 (m, 1H), 3.21-2.93 (m, 3H), 2.61-2.29 (m, 1H), 2.2-1.61 (m, 4H). | 442 (M − 1) $C_{15}H_{21}N_7O_7S$ |
| 28. | | | δ 10.33 (s, 1H), 10.17 (s, 1H), 8.473 (s, 1H), 7.61 (d, 1H), 7.34 (d, 1H), 5.13 (m, 1H), 4.42-4.22 (m, 1H), 4.04 (m, 1H), 3.89-3.87 (m, 1H), 3.73-3.56 (m, 1H), 3.44-3.38 (m, 2H), 3.24-3.19 (m, 2H), 3.05-3.02 (m, 2H), 2.96-2.86 (m, 1H), 2.20-1.88 (m, 2H), 1.74-1.46 (m, 2H). | 442 (M − 1) $C_{15}H_{21}N_7O_7S$ |
| 29. | | | δ 10.52 (s, 1H), 10.24 (s, 1H), 9.76 (bs, 1H), 9.21 (bs, 1H), 8.62 (s, 1H), 8.07 (s, 1H), 5.37-5.34 (m, 1H), 4.45-4.43 (m, 1H), 4.04 (bs, 1H), 3.91-3.54 (m, 3H), 3.35-2.96 (m, 3H), 2.39-2.32 (m, 1H), 2.06-1.60 (m, 4H). | 443.1 (M − 1) $C_{14}H_{20}N_8O_7S$ |

TABLE 1-continued

| Example No. | Compound of Formula (I) | Compound of Formula (IX) | $^1$H NMR (DMSO-$d_6$) | Mass (as free acid) Molecular Formula |
|---|---|---|---|---|
| 30. | [structure] | [structure] | δ 10.55 (s, 1H), 10.24 (s, 1H), 9.01 (s, 1H), 7.82 (d, 1H), 7.65 (d, 1H), 5.29-5.26 (m, 1H), 4.47-4.42(m, 1H), 4.05-3.78(m, 3H), 3.64-3.56 (m, 2H), 3.20-3.09 (m, 2H), 3.07-3.02 (m, 2H), 2.34-2.27 (m, 1H), 2.07-2.27 (m, 1H), 2.07-2.01 (m, 1H), 1.89-1.72 (m, 1H), 1.64-1.60 (m, 1H). | 442 (M − 1) $C_{15}H_{21}N_7O_7S$ |
| 31. | [structure] | [structure] | δ 10.52 (s, 1H), 10.22 (s, 1H), 9.80-9.40 (s, 2H), 5.73-5.70 (m, 1H), 4.50-4.45 (m, 1H), 4.03-3.75 (m, 4H), 3.02-3.10 (m, 2H), 3.04-3.02 (m, 1H), 2.66-2.59 (m, 1H), 2.48 (s, 3H), 2.05-1.61 (m, 4H). | 458 (M − 1) $C_{14}H_{21}N_9O_7S$ |
| 32. | [structure] | [structure] | δ = 10.49 (s, 1 H), 10.20 (br s, 1 H), 9.92 (br s, 1 H), 9.18 (s, 1 H), 7.89 (s, 1 H), 7.59 (s, 1 H), 6.34 (s, 1 H), 5.29(s, 1 H), 4.62-4.59 (m, 1 H), 4.04 (s, 1 H), 3.89-3.79 (m, 2 H), 3.62-3.52 (m, 1 H), 3.06-2.03 (m, 1 H), 2.63-1.58 (m, 1 H), 2.45-2.41 (m, 1 H), 2.05-1.82 (m, 2 H), 1.75-1.54 (m, 2 H). | 444.2 (M + 1) $C_{15}H_{21}N_7O_7S$ |
| 33. | [structure] | [structure] | δ 10.41 (s, 1 H), 10.24 (s, 1 H), 8.96 (s, 1 H), 7.82 (s, 1 H), 7.64 (s, 1 H), 5.26-5.21 (m, 1H), 4.58 (t, J = 8.0 Hz, 1 H), 4.05 (s, 1 H), 3.91-3.85 (m, 2 H), 3.60-3.56 (m, 2 H), 3.20-3.14 (m, 1 H), 3.06-3.03 (m, 1H), 2.79-2.72 (m, 1 H), 2.61-2.57 (m, 1 H), 2.05-1.85 (m, 2 H), 1.78-1.59 (m, 2 H). | 442 (M − 1) $C_{15}H_{21}N_7O_7S$ |
| 34. | [structure] ·TFA | [structure] | δ 10.44 (brs, 2H), 10.25 (brs, 2H), 9.13 (s, 1H), 7.89 (s, 1H), 7.73 (s, 1H), 5.14-5.08 (m, 1H). 4.66-4.58 (m, 1H), 4.08-4.04 ( m, 1H), 3.96-3.90 ( m, 2H), 3.68-3.60 (m, 2H), 3.24-3.20 (m, 1H) 3.10-3.04 (m, 1H), 2.96-2.86 (m, 1H), 2.72-2.62 (m, 1H), 2.10-1.56 (m, 4H). | 442.2 (M − 1) $C_{17}H_{22}F_3N_7O_9S$ |

BIOLOGICAL ACTIVITY DATA

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations, (Clinical and Laboratory Standards Institute (CLSI), Performance Standards for Antimicrobial Susceptibility Testing, $20_{th}$ Informational Supplement, M07-A9, Volume 32, No. 2, 2012). Molten Mueller Hinton Agar (BD, USA) containing serial dilutions of each antibacterial agent were poured on to the plates and allowed to solidify. Appropriate suspensions from the freshly grown cultures were prepared in normal saline so that about $10^4$CFU/spot of the organism was delivered on to the drug containing agar plates using automated multipoint inoculator (Mast, UK). The plates were incubated in Biochemical oxygen demand (BOD) incubator at 37° C. for 18 hours and then examined for growth.

Method for the determination of MIC: The Minimum Inhibitory Concentration (MIC) determination for the combinations was carried out in Muller Hinton Agar (MHA) (BD, USA) according to Clinical and Laboratory Standards Institute (CLSI) recommendations, (Clinical and Laboratory Standards Institute (CLSI), Performance Standards for Antimicrobial Susceptibility Testing, 20$^{th}$ Informational Supplement, M 100-S20, Volume 30, No. 1, 2010). In short, the test strains were adjusted to deliver about 10$^4$CFU per spot with a multipoint inoculator (Applied Quality Services, UK). The plates were poured with MHA containing doubling concentration range of representative compounds according to present invention. The plates were inoculated and were incubated at 35° C. for 18 hour. MICs were read as the lowest concentration of drug that completely inhibited bacterial growth. The Table 2 depicts the antibacterial activity profile of compounds according to present invention against various multidrug resistant bacterial strains. These compounds when tested alone exhibited lower MIC values in comparison to standard.

TABLE 2

Antibacterial activity of representative compounds according to invention (expressed as MICs (mcg/ml))

| Compounds | K. pneumoniae ATCC 700603 | E. coli 13351 | E. coli 13352 | E. coli 13353 | E. coli M 36 | E. coli 7 MP | E. coli M 49 | E. coli M 50 |
|---|---|---|---|---|---|---|---|---|
| Example 1 | >32 | 4 | 4 | 2 | 1 | 8 | 16 | 2 |
| Example 2 | >32 | 1 | 1 | 1 | 1 | 2 | 4 | 1 |
| Example 3 | >32 | 1 | 1 | 1 | 2 | 8 | 4 | 1 |
| Example 4 | >32 | 4 | 2 | 2 | 2 | 4 | 8 | 2 |
| Example 5 | >32 | 1 | 1 | 1 | 1 | 2 | 8 | 1 |
| Example 6 | >32 | 2 | 2 | 1 | 1 | 4 | 8 | 1 |
| Example 7 | >32 | 1 | 1 | 0.5 | 0.5 | 2 | 4 | 1 |
| Example 8 | >32 | 1 | 1 | 0.5 | 0.5 | 2 | 4 | 1 |
| Example 9 | >32 | 2 | 2 | 1 | 1 | 2 | 4 | 1 |
| Example 10 | >32 | 2 | 2 | 1 | 1 | 4 | 4 | 1 |
| Example 11 | >32 | 4 | 2 | 2 | 2 | 8 | 16 | 2 |
| Example 12 | >32 | 4 | 2 | 2 | 2 | 8 | 16 | 2 |
| Example 13 | >32 | 2 | 2 | 1 | 1 | 4 | 8 | 2 |
| Example 14 | >32 | 4 | 4 | 2 | 2 | 4 | 8 | 2 |
| Example 16 | >32 | 2 | 2 | 2 | 2 | 8 | 8 | 2 |
| Example 17 | >32 | 8 | 8 | 4 | 4 | 16 | 16 | 8 |
| Example 18 | >32 | 2 | 2 | 1 | 2 | 4 | 16 | 2 |
| Example 19 | >32 | 8 | 8 | 4 | 8 | >32 | 32 | 8 |
| Example 20 | >32 | 8 | 16 | 8 | 4 | 16 | 16 | 8 |
| Example 21 | >32 | 8 | 8 | 4 | 4 | 16 | 16 | 8 |
| Example 22 | >32 | 8 | 16 | 4 | 4 | 16 | 8 | 8 |
| Example 23 | >32 | 2 | 2 | 1 | 1 | 4 | 8 | 1 |
| Example 24 | >32 | 2 | 2 | 4 | 4 | 8 | 16 | 4 |
| Example 25 | >32 | 1 | 1 | 0.5 | 1 | 2 | 8 | 1 |
| Example 26 | >32 | 2 | 2 | 2 | 4 | 8 | >32 | 4 |
| Example 27 | >32 | 1 | 1 | 1 | 1 | 8 | >32 | 1 |
| Example 28 | >32 | 1 | 1 | 1 | 1 | 4 | 8 | 2 |
| Example 29 | >32 | 1 | 1 | 0.5 | 0.5 | 2 | 4 | 0.5 |
| Example 30 | >32 | 4 | 8 | 4 | 4 | 16 | 16 | 4 |
| Example 31 | >32 | 4 | 4 | 4 | 4 | 16 | >32 | 8 |
| Example 32 | >32 | 4 | 4 | 4 | 4 | 16 | 32 | 4 |
| Example 33 | >32 | 4 | 4 | 4 | 2 | 8 | 16 | 2 |
| Example 34 | >32 | 4 | 8 | 4 | 4 | 16 | 4 | 8 |
| Ceftazidime | 16 | 16 | >32 | >32 | >32 | >32 | >32 | >32 |

| Compounds | E. coli M 138 | P. mirabilis S 137B | E. coli H 483 | K. pneumoniae H 521 | K. pneumoniae H 522 | K. pneumoniae H 523 | K. pneumoniae H 525 |
|---|---|---|---|---|---|---|---|
| Example 1 | 4 | >32 | — | 4 | 4 | 4 | 4 |
| Example 2 | 1 | — | — | 1 | 1 | 1 | 1 |
| Example 3 | 2 | >32 | — | 4 | 4 | 4 | 4 |
| Example 4 | 2 | >32 | >32 | 4 | 4 | 4 | 4 |
| Example 5 | 1 | >32 | — | 4 | 4 | 4 | 4 |
| Example 6 | 1 | >32 | — | 2 | 2 | 2 | 2 |
| Example 7 | 1 | >32 | — | 2 | 2 | 2 | 2 |
| Example 8 | 1 | >32 | — | 1 | 1 | 1 | 1 |
| Example 9 | 1 | >32 | — | 2 | 2 | 2 | 2 |
| Example 10 | 1 | >32 | >32 | 2 | 2 | 2 | 2 |
| Example 11 | 2 | >32 | >32 | 4 | 4 | 4 | 2 |
| Example 12 | 2 | >32 | >32 | 4 | 4 | 4 | 4 |
| Example 13 | 1 | >32 | >32 | 2 | 2 | 2 | 2 |
| Example 14 | 2 | >32 | >32 | 4 | 4 | 4 | 4 |
| Example 16 | 2 | >32 | >32 | 4 | 4 | 4 | 4 |
| Example 17 | 4 | — | — | 8 | 8 | 8 | 8 |
| Example 18 | 2 | — | — | 2 | 2 | 2 | 2 |
| Example 19 | 8 | — | — | 8 | 8 | 8 | 8 |
| Example 20 | 4 | — | — | 8 | 8 | 8 | 8 |
| Example 21 | 4 | — | — | 8 | 4 | 4 | 8 |
| Example 22 | 8 | — | — | 8 | 8 | 8 | 8 |
| Example 23 | 2 | >32 | — | 4 | 4 | 4 | 4 |
| Example 24 | 4 | >32 | — | 4 | 4 | 4 | 4 |

TABLE 2-continued

Antibacterial activity of representative compounds according to invention (expressed as MICs (mcg/ml))

| | | | | | | | |
|---|---|---|---|---|---|---|---|
| Example 25 | 2 | >32 | — | 4 | 4 | 4 | 8 |
| Example 26 | 4 | >32 | — | 8 | 8 | 16 | 16 |
| Example 27 | 2 | >32 | — | 4 | 4 | 4 | 4 |
| Example 28 | 2 | >32 | — | 4 | 4 | 4 | 4 |
| Example 29 | 1 | >32 | — | 2 | 2 | 2 | 2 |
| Example 30 | 8 | >32 | — | 2 | 2 | 2 | 2 |
| Example 31 | 8 | >32 | — | 16 | 16 | 16 | 8 |
| Example 32 | 4 | >32 | — | 8 | 8 | 8 | 8 |
| Example 33 | 4 | >32 | — | 8 | 4 | 4 | 4 |
| Example 34 | — | >32 | — | 8 | 8 | 8 | 8 |
| Ceftazidime | >32 | >32 | >32 | >32 | >32 | >32 | >32 |

The invention claimed is:

1. A compound of Formula (I):

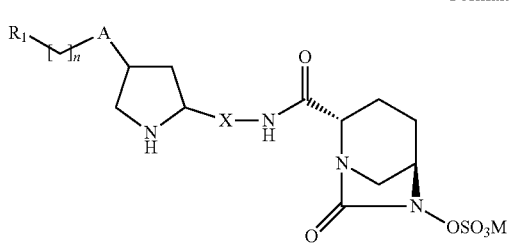

Formula (I)

or a stereoisomer or a pharmaceutically acceptable salt thereof; wherein:

X is selected from —$CH_2$—O- or —(C=O)—NH—;

A is heterocycloalkyl or heteroaryl optionally substituted with one or more substituents selected from $C_1$-$C_6$ alkyl, $NR_2R_3$, aryl, heteroaryl, cycloalkyl or heterocycloalkyl;

$R_1$ is selected from:
(a) hydrogen,
(b) $C_1$-$C_6$ alkyl optionally substituted with one or more substituents independently selected from $OR_2$, $NR_2R_3$, $SR_2$, halogen, CN, $COOR_2$, $CONR_2R_3$, $SR_2$, $CH_2OR_2$ or $CH_2NR_2R_3$, aryl, heteroaryl, cycloalkyl or heterocycloalkyl,
(c) halogen,
(d) CN,
(e) $CONR_2R_3$,
(f) $COOR_2$,
(g) CHO,
(h) $NR_2R_3$,
(i) $NHCOOR_2$,
(j) $SR_2$,
(k) $SOR_2$,
(l) $SO_2R_2$,
(m) aryl,
(n) heteroaryl,
(o) cycloalkyl, or
(p) heterocycloalkyl;

$R_2$ and $R_3$ are each independently selected from:
(a) hydrogen,
(b) $C_1$-$C_6$ alkyl,
(c) cycloalkyl,
(d) heterocycloalkyl,
(e) aryl, or
(f) heteroaryl;

n is 0, 1, 2, 3 or 4;

M is hydrogen or a cation.

2. The compound according to claim 1, selected from:
(2S,5R)—N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-tetrazol-1-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(2H-1,2,3-triazol-2,1)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;
(2S,5R)-N-{[(2 R,4S)-4-(2H-tetrazol-2-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(1H-tetrazol-1-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(2H-1,2,3-triazol-2-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;
(2S,5R)-N-{[(2R,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(1H-pyrrol-1-yl)pyrrolidin-2-yl]methyloxy}-7-oxo-6-(sulfooxy)-1,6-diazabicyclo[3.2.1]octane-2-carboxamide;
(2S,5R)-N-{[(2S,4R)-4-(1H-pyrrol-1-yl)pyrrolidin-2-yl]methyloxy}-7-oxo-6-(sulfooxy)-1,6-diazabicyclo[3.2.1]octane-2-carboxamide;
(2S,5R)-N-{[(2S,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-tetrazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-pyrrole-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2H-tetrazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-tetrazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(piperidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(piperazin-1-yl)pyrrolidi n-2-yl]methyloxy}-7-oxo-6-(sulfooxy)-1,6-diazabicyclo[3.2.1]octane-2-carboxamide;

(2S,5R)-N-{[(2 R,4R)-4-(piperazin-1-yl)pyrrolidi n-2-yl]methyloxy}-7-oxo-6-(sulfooxy)-1,6-diazabicyclo[3.2.1]octane-2-carboxamide;

(2S,5R)-N-{[(2 R,4S)-4-(piperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(4-methylpiperazin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2 R,4R)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2 R,4S)-4-(morpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2 S,4R)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2 R,4R)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2 R,4S)-4-(thiomorpholin-4-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(azeditin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5 R)-N-{[(2R,4S)-4-(pyrrolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5 R)-N-{[(2S,4S)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(pyrazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(imidazolidin-1-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2S,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2S,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

(2S,5R)-N-{[(2R,4S)-4-[4-({[(2S)-1-hydroxypropan-2-yl]amino}methyl)piperidin-1-yl] pyrrolidin-2-yl]methoxy}-7-oxo-6-(sulfooxy)-1,6-diazabicyclo[3.2.1]octane-2-carboxamide;

(2S,5R)-N'-{[(2S,4S)-4-(1H-tetrazol-1-yl)pyrrolidin-2-yl]carbonyl}-7-oxo-6-(sulfooxy)--1,6-diazabicyclo[3.2.1]octane-2-carbohydrazide;

(2S,5R)-N'-{[(2S,4S)-4-(2H-tetrazol-2-yl)pyrrolidin-2-yl]carbonyl}-7-oxo-6-(sulfooxy)-1,6-diazabicyclo[3.2.1]octane-2-carbohydrazide;

(2S,5R)-N'-{[(2S,4S)-4-(5-methyl-2H-tetrazol-2-yl)pyrrolidin-2-yl]carbonyl}-7-oxo-6-(sulfooxy)-1,6-diazabicyclo[3.2.1]octane-2-carbohydrazide;

(2R,5R)-N'-{[(2S,4S)-4-(2H-1 ,2,3-triazol-2-yl)pyrrolidin-2-yl]carbonyl}-7-oxo-6-(sulfooxy)- -1,6-diazabicyclo[3.2.1]octane-2-carbohydrazide;

(2R,5R)-N'-{[(2S,4S)-4-(1H-1 ,2,3-triazol-1-yl)pyrrolidin-2-yl]carbonyl}-7-oxo-6-(sulfooxy)-1,6-diazabicyclo[3.2.1]octane-2-carbohydrazide;

(2R,5R)-7-oxo-6-(sulfooxy)-N'-{[(2S,4S)-4-(1H-1 ,2,4-triazol-1-yl)pyrrolidin-2-yl]carbonyl}-1,6-diazabicyclo[3.2.1]octane-2-carbohydrazide;

(2S,5R)-N'-{[(2S,4S)-4-(1H-imidazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2RS,4S)-4-(1H-imidazol-1-yl) pyrrolidin-2-yl]carbonyl}-7-oxo-6-(sulfooxy)-1,6-diazabicyclo[3.2.1]octane-2-carbohydrazide;

(2S,5R)-N-{[(2S,4R)-4-(1H-pyrazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2SR, 4S)-4-(1H-pyrazol-1-yl)pyrrolidin-2-yl]carbonyl}-7-oxo-6-(sulfooxy)-1,6-diazabicyclo[3.2.1]octane-2-carbohydrazide;

(2S,5R)-N'-{[(2S,4R)-4-(1H-imidazol-1-yl)pyrrolidin-2-yl]carbonyl}-7-oxo-6-(sulfooxy)-1,6-diazabicyclo[3.2.1]octane-2-carbohydrazide; (2S,5R)-N-{[(2R,4S)-4-(1H-imidazol-1-yl)pyrrolidin-2-yl]carbonyl}-7-oxo-6-(sulfooxy)-1,6-diazabicyclo[3.2.1]octane-2-carboxhydrazide;

or a stereoisomer or a pharmaceutically acceptable salt thereof.

3. The compound according to claim 1, selected from:

Sodium salt of (2S,5R)-N-{[(2S,4S)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-pyrrol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-pyrrol-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2S,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-benzimidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-pyrrole-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(1H-pyrrole-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2R,4S)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4S)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-pyrrole-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2H-tetrazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-tetrazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2H-1,2,3-triazol-2-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-1,2,3-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-1,2,4-triazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-1,2-pyrazol-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2R,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2R,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Trifluoroacetate salt of (2S,5R)-N-{[(2S,4R)-4-(4-amino-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(2-methyl-1H-1,3-imidazol-1-yl)pyrrolidin-2-yl]methyloxy}-7-oxo-6-(sulfooxy)-1,6-diazabicyclo[3.2.1]octane-2-carboxamide;

Sodium salt of (2S,5R)-N-{[(2S,4R)-4-(1H-benzimidazol-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(piperidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(piperidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(piperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(4-methylpiperazin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(4-methylpiperazin-1 -yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(4-methylpiperazin-1 -yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(4-methylpiperazin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(morpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(thiomorpholin-4-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(azeditin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-Oxazeditin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(pyrrolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(pyrrolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(pyrazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4R)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2S,4S)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4R)-4-(imidazolidin-1-yl)pyrrolidin-2-yl]methyloxy}-7-oxo-6-(sulfooxy)-1,6-diazabicyclo[3.2.1]octane-2-carboxamide;

Di trifluoro acetic acid salt of (2S,5R)-N-{[(2R,4S)-4-(imidazolidin-1-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-oxazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2S,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4R)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-(1,3-thiazolidin-3-yl)pyrrolidin-2-yl]methyloxy}-7-oxo-6-(sulfooxy)-1,6-diazabicyclo[3.2.1]octane-2-carboxamide;

Trifluoro acetic acid salt of (2S,5R)-N-{[(2R,4S)-4-[4-({[(2S)-1-hydroxypropan-2-yl]amino} methyl)piperidin-1-yl]pyrrolidin-2-yl)methoxy}-7-oxo-6-(sulfooxy)-1,6-diazabicyclo[3.2.1]octane-2-carboxamide;

Sodium salt of (2S,5R)-N'-{[(2S,4S)-4-(1H-tetrazol-1-yl) pyrrolidin-2-yl]carbonyl}-7-oxo-6-(sulfooxy)—1,6-diazabicyclo[3.2.1]octane-2-carbohydrazide;

Sodium salt of (2S,5R)-N'-{[(2S,4S)-4-(2H-tetrazol-2-yl) pyrrolidin-2-yl]carbonyl}-7-oxo-6-(sulfooxy)-1,6-diazabicyclo[3.2.1]octane-2-carbohydrazide;

Sodium salt of (2S,5R)-N'-{[(2S,4S)-4-(5-methyl-2H-tetrazol-2-yl)pyrrolidin-2-yl]carbonyl} -7-oxo -6-(sulfooxy)-1,6-diazabicyclo[3.2.1]octane-2-carbohydrazide;

Sodium salt of (2R,5R)-N'-{[(2S,4S)-4-(2H-1,2,3-triazol-2-yl)pyrrolidin-2-yl]carbonyl}-7-oxo-6-(sulfooxy)--1,6-diazabicyclo[3.2.1]octane-2-carbohydrazide;

Sodium salt of (2R,5R)-N'-{[(2S,4S)-4-(1H-1,2,3-triazol-1-yl)pyrrolidin-2-yl]carbonyl}-7-oxo-6-(sulfooxy)-1,6-diazabicyclo[3.2.1]octane-2-carbohydrazide;

Sodium salt of (2R,5R)-7-oxo-6-(sulfooxy)-N'-{[(2S,4S)-4-(1H-1,2,4-triazol-1-yl)pyrrolidin-2-yl]carbonyl}-1,6-diazabicyclo[3.2.1]octane-2-carbohydrazide;

Sodium salt of (2S,5R)-N'-{[(2S,4S)-4-(1H-imidazol-1-yl)pyrrolidin-2-yl]carbonyl}-7-oxo-6-(sulfooxy)-1,6-diazabicyclo[3.2.1]octane-2-carbohydrazide;

Sodium salt of (2S,5R)-W-{[(2RS,4S)-4-(1H-imidazol-1-yl) pyrrolidin-2-yl]carbonyl}-7-oxo-6-(sulfooxy)-1,6-diazabicyclo[3.2.1]octane-2-carbohydrazide;

Sodium salt of (2S,5R)-N-{[(2S,4R)-4-(1H-pyrazol-1-yl) pyrrolidin-2-yl]carbonyl}-7-oxo-6-(sulfooxy)-1,6-diazabicyclo[3.2.1]octane-2-carbohydrazide;

Sodium salt of (2S,5R)-W-{[(2SR, 4S)-4-(1H-pyrazol-1-yl)pyrrolidin-2-yl]carbonyl}-7-oxo-6-(sulfooxy)-1,6-diazabicyclo[3.2.1]octane-2-carbohydrazide;

Trifluoro acetic acid salt of (2S,5R)-N'-{[(2S,4R)-4-(1H-imidazol-1-yl)pyrrolidin-2-yl]carbonyl}-7-oxo-6-(sulfooxy)-1,6-diazabicyclo[3.2.1]octane-2-carbohydrazide;

Trifluoro acetic acid salt of (2S,5R)-N-{[(2R,4S)-4-(1H-imidazol-1-yl)pyrrolidin-2-yl]carbonyl}-7-oxo-6-(sulfooxy)-1,6-diazabicyclo[3.2.1]octane-2-carboxhydrazide; or a stereoisomer thereof.

4. The compound of Formula (I) according to claim 1, wherein X is —CH$_2$—O—.

5. The compound of Formula (I) according to claim 1, wherein X is —(C=O)—NH—.

6. The compound of Formula (I) according to claim 1, wherein A is heterocycloalkyl.

7. The compound of Formula (I) according to claim 1, wherein A is heteroaryl.

8. The compound of Formula (I) according to claim 1, wherein A is heteroaryl linked to pyrrolidine through "N" of heteroaryl.

9. The compound of Formula (I) according to claim 1, wherein A is heterocycloalkyl linked to pyrrolidine through "N" of heterocycloalkyl.

10. A pharmaceutical composition comprising a compound of Formula (I) according to claim 1, for use in prevention or treatment of bacterial infection.

11. The pharmaceutical composition according to claim 10, further comprising at least one antibacterial agent or a pharmaceutically acceptable salt thereof.

12. The pharmaceutical composition according to claim 11, wherein the antibacterial agent is selected from a group consisting of aminoglycosides, ansamycins, penems, carbapenems, carbacephems, cephalosporins, cephamycins, lincosamides, lipopeptides, macrolides, monobactams, nitrofurans, penicillins, polypeptides, quinolones, sulfonamides, tetracyclines, and oxazolidinone antibacterial agents.

13. The pharmaceutical composition according to claim 11, wherein the antibacterial agent is a beta-lactam antibacterial agent.

14. The pharmaceutical composition according to claim 11, wherein the antibacterial agent is selected from a group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoximeaxetil, cefpodoximeproxetil, cefterampivoxil, cefetametpivoxil, cefcapenepivoxil or cefditorenpivoxil, cefuroxime, cefuroxime axetil, loracarbacef, ceftaroline, ceftolozane, latamoxef, piperacillin, imipenem, doripenem, and meropenem.

15. A method for preventing or treating a bacterial infection in a subject, said method comprising administering to said subject a pharmaceutically effective amount of a compound according to claim 1.

16. A method for preventing or treating a bacterial infection in a subject, said method comprising administering to said subject a pharmaceutically effective amount of a compound according to claim 11.

* * * * *